United States Patent [19]

Pfrengle

[11] Patent Number: 5,641,883

[45] Date of Patent: Jun. 24, 1997

[54] FUNGICIDAL SPIROHETEROCYCLIC DERIVATIVES

[75] Inventor: Waldemar Franz Augustin Pfrengle, Seibersbach, Germany

[73] Assignee: American Cyanamid Co., Madison, N.J.

[21] Appl. No.: 462,083

[22] Filed: Jun. 5, 1995

Related U.S. Application Data

[62] Division of Ser. No. 278,447, Jul. 21, 1994.

[30] Foreign Application Priority Data

Jul. 22, 1993 [EP] European Pat. Off. ............ 93111733

[51] Int. Cl.[6] .................. C07D 307/94; C07D 405/04; C07D 413/04
[52] U.S. Cl. .................. 544/70; 546/15; 549/331
[58] Field of Search ................ 549/331; 546/15; 544/70

[56] References Cited

U.S. PATENT DOCUMENTS

| 4,800,202 | 1/1989 | Weissmüller et al. .......... 514/227 |
|---|---|---|
| 5,175,295 | 12/1992 | Zipplies et al. ............... 546/15 |

FOREIGN PATENT DOCUMENTS

| 0278352 | 8/1988 | European Pat. Off. . |
|---|---|---|
| 0281842 | 9/1988 | European Pat. Off. . |
| 0349247 | 1/1990 | European Pat. Off. . |
| 0413223 | 2/1991 | European Pat. Off. . |
| WO-A-9216518 | 10/1992 | WIPO . |

OTHER PUBLICATIONS

Kiyoshima Y., *Spiro compounds*, vol. 84, No. 9, 1 Mar. 1976.
Colonge, j., et a;., "No. 13–Sur quelgue y–glycols acetyleniques promaires–tertiaires et quelques–uns de leurs derives," in Memories Presentes A La Societe Chemique, pp. 211–218 (1957). Month of Publication Not Provided.

*Primary Examiner*—Mukund J. Shah
*Assistant Examiner*—King Lit Wong
*Attorney, Agent, or Firm*—Gregory M. Hill

[57] ABSTRACT

New fungicidal spiroheterocyclic compounds are described, having the general formula I,

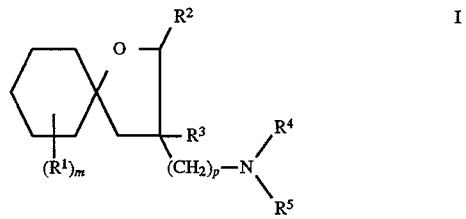

or an acid-addition salt thereof, in which
$R^1$, $R^2$, $R^3$, $R^4$ and $R^5$ are as defined in the specification. A process of preparing such compounds is also described.

1 Claim, No Drawings

FUNGICIDAL SPIROHETEROCYCLIC DERIVATIVES

This is a divisional application of Ser. No. 08/278,447, filed Jul. 24, 1994.

The present invention relates to certain new spiroheterocyclic compounds having fungicidal properties, processes for the preparation of these compounds, fungicidal compositions containing the compounds and the use of the compounds as fungicides for the control of phytopathogenic fungi.

In EP 281842, EP 349247, EP 413223 and WO 92/16518 fungicidal spiroheterocyclic compounds have been described. These known compounds contain a substituted cyclohexyl ring in spiro conjunction with a substituted heterocyclic five or six membered ring. The substituents of the cyclohexyl ring are usually (substituted) (branched) alkyl or phenyl groups. The substituents of the heterocyclic ring are usually (substituted) (cyclo)alkyl- or dialkyl-aminomethyl or dialkyl-amino-polymethyl groups, including alkylene-amino-methyl or alkylene-amino-polymethyl groups.

It has now been found that certain new spiroheterocyclic compounds show excellent fungicidal activity against certain phytopathogenic fungi, for instance against *Plasmopora viticola*, *Botrytis cinera*, *Erysiphe graminis*, *Pseudocercosporella herpotrichoides*, *Rhizoctonia solani*, *Venturia inaequalis* and *Alternaria solani*.

The present invention therefore relates to compounds of the general formula I

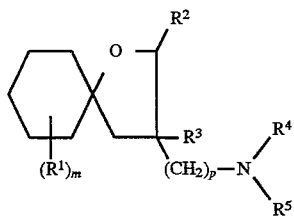

or an acid-addition salt thereof, in which $R^1$ or each $R^1$ independently represents an optionally substituted alkyl, cycloalkyl, cycloalkylalkyl, alkoxy, cycloalkoxy, alkoxyalkyl, aralkyl, aryl or aryloxy group, or $R^1$ or each $R^1$, together with the ring to which they are attached, represents an optionally substituted polycyclic hydrocarbyl group, $R^2$ represents a hydrogen atom or a $C_{1-4}$ alkyl group, $R^3$ represents a hydrogen atom, a hydroxy group or an optionally substituted alkoxy or acyloxy group, $R^4$ and $R^5$ each independently represent a hydrogen atom, an optionally substituted alkyl, alkenyl, alkynyl, cycloalkylalkyl, cycloalkyl, bicycloalkyl, tricycloalkyl, alkoxyalkyl, aryl, aralkyl, haloaralkyl, a 4- to 6- member heterocyclyl, tetrahydrofurfuryl or dioxolanyl group, or $R^4$ and $R^5$ together represent an optionally substituted, saturated or unsaturated carbon chain which may optionally contain one or more oxygen atoms and which may optionally be aryl- or cycloalkyl-fused, m represents zero or an integer from 1 to 6, and p represents zero or an integer from 1 to 3.

The invention especially relates to compounds of the general formula I in which any alkyl part of any of the groups $R^1$ to $R^5$ contains up to 12 carbon atoms, preferably up to 10 carbon atoms, more preferably up to 9 carbon atoms, any alkenyl or alkynyl part of any of the substituents $R^1$ to $R^5$ contains up to 12 carbon atoms, preferably up to 10 carbon atoms, more preferably up to 8 carbon atoms, any cycloalkyl part of any of the substituents $R^1$ to $R^5$ contains from 3 to 10 carbon atoms, preferably from 3 to 8 carbon atoms, more preferably from 3 to 6 carbon atoms, any bicyclic, tricyclic or polycyclic part of the groups $R^1$ to $R^5$ contains from 6 to 12, from 8–14, respectively from 6 to 20 carbon atoms, any saturated or unsaturated chain, especially carbon chain, contains from 3 to 10 chain members, preferably from 4 to 6 carbon atoms, and any aryl part of any of the substituents $R^1$ to $R^5$ contains 6, 10 or 14 carbon atoms, preferably 6 or 10 carbon atoms, and in which each optionally substituted group independently is substituted by one or more halogen atoms or nitro, cyano, alkyl, preferably $C_{1-6}$ alkyl, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, halo- or dihalo-phenyl or pyridyl groups. Any alkyl, alkenyl or alkynyl group may be linear or branched. A 4- to 6- membered heterocyclic group may be any heterocyclic group with 4 to 6 ring atoms, interrupted by one or more heteroatoms selected from sulfur, nitrogen, and oxygen, preferably oxygen. A halogen atom suitably denotes a fluorine, chlorine or bromine atom.

The invention especially relates to compounds of the general formula I in which $R^1$ or each $R^1$ independently represents a $C_{1-10}$ alkyl, $C_{3-6}$ cycloalkyl, $C_{3-8}$ cycloalkyl-$C_{1-6}$ alkyl, $C_{1-6}$ alkoxy, $C_{1-10}$ alkoxy-$C_{1-6}$ alkyl or phenyl group, or one or more groups $R^1$ together with the ring to which they are attached, represent a $C_{7-20}$ polycyclic group, preferably a $C_{8-12}$ bicyclic, $C_{9-14}$ tricyclic or $C_{9-16}$ quadricyclic hydrocarbyl group, preferably a saturated hydrocarbyl group, each of the above groups optionally substituted by one or more halogen atoms, especially chlorine and/or fluorine atoms, or $C_{1-4}$ alkyl, $C_{1-4}$ haloalkyl or $C_{1-4}$ alkoxy groups. Preferably $R^1$ or each $R^1$ independently represents a $C_{1-8}$, suitably $C_{1-6}$, alkyl group, especially a branched alkyl group, more especially secondary and tertiary alkyl groups as secondary butyl, tertiary butyl and tertiary amyl groups. More preferably, $R^1$ or each $R^1$ independently represents a t-butyl or t-amyl group. The invention also especially relates to compounds of the general formula I in which m represents an integer from 1 to 4, preferably 1 or 2, more preferably 1. The group or groups $R^1$ are preferably attached to the positions 3, 4 and/or 5 of the cyclohexyl ring, more preferably to the 4-position.

The invention also especially relates to compounds of the general formula I in which $R^2$ represents a hydrogen atom or a methyl group, preferably a hydrogen atom.

The invention further especially relates to compounds of the general formula I in which $R^3$ represents a hydrogen atom.

The invention further especially relates to compounds of the general formula I in which $R^4$ and $R^5$ each independently represent a hydrogen atom, a $C_{1-20}$ alkyl, especially $C_{3-10}$ alkyl, $C_{2-6}$ alkenyl, $C_{2-6}$ alkynyl, $C_{3-8}$ cycloalkyl-$C_{1-6}$ alkyl, $C_{3-8}$ cycloalkyl, $C_{6-10}$ bicycloalkyl, $C_{8-14}$ tricycloalkyl, phenyl, phenyl-$C_{1-6}$ alkyl, especially benzyl, halophenyl-$C_{1-6}$ alkyl or pyridyl-$C_{1-6}$ alkyl group, or $R^4$ and $R^5$ together represent a saturated carbon chain containing three to eight carbon atoms while optionally one or more additional oxygen atoms may be present in the chain and which chain may optionally be aryl- or cycloalkyl-fused. Preferably $R^4$ and $R^5$ each independently represent a hydrogen atom, a $C_2-C_{12}$ alkyl, $C_{2-5}$ alkenyl, $C_{5-7}$ cyclo-$C_{1-2}$ alkyl, $C_{5-7}$ cycloalkyl, $C_{8-10}$ bicycloalkyl or phenyl-$C_{1-2}$ alkyl group, or $R^4$ and $R^5$ together represent a saturated chain containing four or five carbon atoms while optionally additional oxygen atoms may be present and which chain optionally may be aryl- or cycloalkyl-fused, especially cyclopentyl, cyclohexyl or cycloheptyl fused, each of the above groups optionally substituted by one or more halogen atoms, especially chlorine and/or fluorine atoms, or $C_{1-4}$ alkyl, $C_{1-4}$ haloalkyl, $C_{4-6}$ cycloalkenyl or $C_{1-4}$ alkoxy groups.

The invention especially relates to compounds of the general formula I in which p represents 0, 1 or 2.

A particular preferred sub-group of compounds of the general formula I is that in which $R^1$ represents a butyl, pentyl or phenyl group, especially a t-butyl or t-pentyl group. Another particular sub-group is that in which $R^2$ represents a hydrogen atom. Another particular sub-group is that in which $R^3$ represents a hydrogen atom. Yet another particular sub-groups is that in which $R^4$ and $R^5$ each independently represent a hydrogen atom or a linear or branched $C_{1-17}$ alkyl group, especially a $C_{1-10}$ alkyl group, an allyl, $C_{3-7}$ cycloalkyl optionally fused with a cyclohexyl group, benzyl or phenyl group, or $R^4$ and $R^5$ together represent a saturated $C_{4-7}$ carbon chain, especially a $C_{4-6}$ carbon chain, which optionally may contain an additional oxygen atom and which optionally may be fused with a cyclohexyl ring, each of the above groups optionally substituted by a fluorine, chlorine or bromine atom or one or two methyl groups, a t-butyl, cyclohexyl, cyclohexenyl, phenyl or pyridyl group.

The present invention further provides a process for the preparation of compounds of the general formula I as defined hereinbefore or acid-addition salts thereof, in which $R^3$ represents a hydrogen atom and p represents zero, which process comprises reaction of a compound of the general formula II

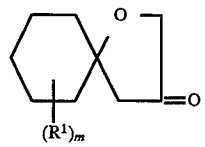

in which $R^1$ and m are as defined hereinbefore, with a compound of the general formula III

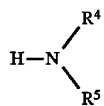

in which $R^4$ and $R^5$ are as defined hereinbefore, under reducing conditions.

Suitable reducing conditions for the reductive amination are well known in the literature. See for instance J. March, Advanced Organic Chemistry, J. Whiley & Sons, New York, 1985. Suitable reducing agents are formic acid (Leuckart-Wallach reduction), complex metal hydrides such as cyanoboro hydride and hydrogen gas together with a hydrogenation catalyst, e.g. Raney nickel.

Some of the starting compounds II are known in the literature. See for instance Bull. Chim. Soc. France, 1958, 211 and Bull. Chim. Soc. France, 1974 (12), 2889–2891. New starting compounds of the general formula II, which form a feature of the invention, may be prepared in the same way as the known compounds as discussed before.

Starting compounds of the general formula III are well known in the literature, and many of them are commercially available.

The reductive amination process of the present invention is suitably carried out in the presence of an organic solvent, for example an ether, an alcohol or a carboxylic acid such as acetic acid.

The process is suitably carried out at a temperature in the range of 0° to 150° C., especially between 40° and 120° C., in the case of formic acid as reducing agent or at temperatures between 0° and 50° C. in the case of complex borohydrides as reducing agents.

In an alternative process for the preparation of the compounds of the present invention the starting compound II is first converted into the corresponding 3-amino-1-oxaspiro (4,5)decane compound, for instance by reaction with hydroxylamine followed by reduction of the obtained oxime. The 3-amino compound is thereafter alkylated, especially with a ketone or aldehyde under suitable reducing conditions or with an alkylating agent. The reaction of the ketone starting material and hydroxylamine is well known in the literature. The reaction may be carried out in an organic solvent/water mixture at temperature between 20° and 100° C. The reducton of the oxime compounds is also well known in the literature. The reduction can be carried out with complex metal hydrides, for instance lithium aluminium hydride, in an organic solvent, e.g. tetrahydrofuran, at temperatures between 40° and 80° C. The alkylation of amines using ketones or aldehydes is well known in the literature, and is described hereinbefore. The alkylation using alkylating agents is also well known in the literature. Alkylating agents, for instance (substituted) alkyl halides may be used in suitable, inert organic solvents at temperatures between 40° and 100° C.

The present invention also provides a process for the preparation of compounds of the general formula I as defined hereinbefore, or acid additon salts thereof, and in which $R^3$ represents a hydroxy, an alkoxy or an acyloxy group and p represents 1, which process comprises reaction of a compound of the general formula II as defined hereinbefore, with hydrogen cyanide or a salt thereof, followed by reduction of the obtained cyanohydrine and alkylation, especially with a ketone or aldehyde under suitable reducing conditions or an alkylating reagent, optionally followed by alkylation or acylation of the 3-hydroxy group. The reaction of the ketone starting material and hydrogen cyanide or a salt thereof can be carried out according to methods well known in the literature, for instance by reaction with sodium- or potassium cyanide at temperatures between 0° and 100° C., especially ambient temperature, in an organic solvent as an alcohol. The reduction of cyanohydrines is also well known in the literature, and can be performed using hydrogen and a noble metal catalyst, e.g. platinum or palladium. The alkylation of the 3-aminomethyl group may be carried out as described hereinbefore. Alkylation and acylation of the 3-hydroxy group can be done as described in the literature for the alkylation or acylation of tertiary alcohols.

The present invention also provides a process for the preparation of compounds of the general formula I as defined hereinbefore, or acid addition salts thereof, and in which $R^3$ represents a hydrogen atom and p represents 1, which process comprises reduction of a compound of the general formula II as defined hereinbefore to an alcohol, activation of the alcohol, followed by reaction with hydrogen cyanide or a salt thereof, reduction of the cyanide group and alkylation of the amine obtained, especially with a ketone or aldehyde under suitable reducing conditions or an alkylating reagent. The reduction of the carbonyl group of the starting compound of the general formula II can be carried out according to methods well known in the literature, for instance by reduction with a complex metal hydride such as sodium borohydride. The activation of the alcohol is also well described in the literature, and may be carried out by reaction with a sulfonylchloride. The substitution of the activated hydroxy group is suitably carried out in a polar organic solvent, for instance an alcohol, an ether or a ketone, using hydrogen cyanide or a salt thereof. The reduction of the cyano group and the alkylation thereof can be carried out as described hereinbefore.

The present invention also provides a process for the preparation of a compound of the general formula I as defined hereinbefore, or acid addition salts thereof, and in which $R^3$ represent a hydrogen atom and p represents 2, which process comprises reaction of a compound of the general formula II as defined hereinbefore, with cyanoacetic acid followed by reduction of the compound obtained into an amine, and alkylation of the amine, especially with a ketone or aldehyde under suitable reducing conditions or an alkylating agent. The reaction of the ketone starting material and cyanoacetic acid is suitably carried out in a polar organic solvent such as pyridine. The reduction of the cyano group and the alkylation of the 3-aminoethyl group may be carried out as described hereinbefore.

Suitably all reactions are carried out using substantially equimolar amounts of the reactants. However, it can be expedient to use one reactant in excess.

It will be appreciated that in addition to the above described reaction steps additional chemical modifications can be made to the compounds and intermediates, e.g. introduction or amendment of certain substituents, additional alkylation reactions etc.

The invention also provides fungicidal compositions comprising at least one of the compounds according to general formula I or an acid addition salt thereof, as well as methods of combating fungi at a locus comprising treatment of the locus with a compound of formula I or an acid addition salt thereof as defined hereinbefore, or with a composition as defined in this specification. The locus to be treated especially comprises plants subject to or subjected to fungal attack, seeds of such plants or the medium in which the plants are growing or are to be grown.

The fungicidal composition comprises a carrier and, as active ingredient, a compound of the general formula I or an acid addition salt thereof.

A method of making such a composition is also provided, which comprises bringing a compound of the general formula I as defined above or an acid addition salt thereof into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

The invention further relates to the use as a fungicide of a compound of formula I as defined hereinbefore or a composition as defined hereinbefore.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The present invention still further provides the use as a fungicide of a compound of the general formula I as defined above or a composition as defined above.

The present invention is of wide applicability in the protection of crop plants against fungal attack. Typical crops which may be protected include cereals, especially wheat and barley, rice, vines, potatoes, tomatoes, top fruit, especially apples, and cucumber. The duration of protection is normally dependent on the individual compound selected, and also a variety of external factors, such as climate, whose impact is normally mitigated by the use of a suitable formulation. The compounds of the present invention are especially suitable to combat *Erysiphe graminis* in cereals.

The invention is further illustrated by the following examples.

EXAMPLES 1–180

3-Amino-1-oxaspiro(4,5)decane derivatives (i) Starting materials

1-Oxaspiro(4,5)decane-3-one and 8-t-butyl-1-oxaspiro(4, 5)-decane-3-one were prepared as decribed in the literature (J. Cologne, R. Falcotet and R. Gaumont, Bull. Soc. Chim. France, 1958, 211 and P. Picard and J. Moulines, Bull Soc. Chim. France, 1974 (12), 2889). New substituted 1-oxaspiro (4.5)decane-3-ones were prepared according to the same method (8-phenyl-1-oxaspiro(4,5)-decane-3-one (m.p. 40°–65° C.; mixture of cis and trans diastereoisomer (4:1); $^1$H NMR (CDCl3): 4.02*(s,2H), 3.95(s,2H); 2.33*(s,2H); 2.25(s,2H); 1.90(m,2H); 1.63-1.35(m,6H); 1.25(dd,2H); 1.10(m, 1H); 0.80(s,9H); 0.77*(s,9H); where signals are separated the minor (trans) diastereoisomer is indicated by an asterisk.); 8-(2-(2-methylbutyl))-1-oxaspiro(4,5)decane-3-one) (b.p. 80°–82° C./0.05 mbar; $^1$H NMR (CDCl$_3$) (cis isomer, obtained from the cis/trans mixture by crystallisation from light petroleum): 7.25(m,5H); 4.02(s,2H); 2.53(m,$^1$H); 2.34(s,2H); 2.07-1.55(m,8H); 6,8,10-(trimethylenemethane)- 1-oxaspiro(4,5)decane-3-one (starting from adamantanone; m.p. 56°–57° C.)), 8-t-butyl-3-methyl-1-oxaspiro- (4,5)decane-3-one (b.p. 70°–80° C./0.04 mbar); 8-(2-(2,4,4-trimethyl-pentyl))-1-oxaspiro(4, 5)decan-3-one ($n_D^{22}$ 1.4834) 8-(2-(2-cyclohexylpropyl))-1-oxaspiro(4,5)decane-3-one (m.p. 63°–69° C.).

(ii) Preparation of 3-Amino-1-oxaspiro(4,5)decane derivatives

The title compounds were prepared by dissolving the (substituted) 1-oxaspiro(4,5)decane-3-one (10 mmol), an amine (10.5 mmol) and zinc chloride (0.7 g, 5.2 mmol) in 25 ml dry methanol. Sodium cyano-borohydride (0.75 g, 12 mmol) was then added and the reaction mixture was stirred overnight. The solvent was distilled off in vacuo and the residue was taken up in ethylacetate (50 ml), washed with 1N sodium hydroxide (100 ml) and water (100 ml). The organic layer was dried with magnesium sulphate, filtered and the solvent was distilled off in vacuo. The resulting oil was purified by chromatography on silica with toluene/20% ethylacetate. Evaporation of the product containing fractions yield the desired compounds, usually in yields between 40 and 80%. In some cases Raney nickel and hydrogen were used, (compound 2: 8-t-butyl-1-oxaspiro(4,5)decane-3-one (10.5 g, 50 mmol) and n-hexylamine (5.5 g, 55 mmol) in methanol (50 ml) was hydrogenated on Raney Nickel (10.0 g, slurried with methanol) at 60° C. After hydrogen uptake had ceased the catalyst was filtered off and washed with methanol. Evaporation of the solvent and distillation of the residue (14.8 g) yielded compound No. 2 as a colourless oil (9.0 g). It was further purified by flash chromatography (silica, toluene/ethylacetate 1:1)).

Compounds according to the invention were prepared as detailed in Table 1 below. In this table, the compounds are identified by reference to formula I.

TABLE I$^{1,2}$

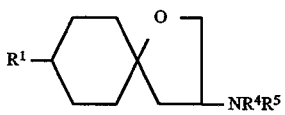

| | $R^1$ | $R^4$ | $R^5$ | ACID |
|---|---|---|---|---|
| 1 | -t-C$_4$H$_9$ | —H | —CH$_2$C$_6$H$_4$-4-Cl | |
| 2 | -t-C$_4$H$_9$ | —H | —(CH$_2$)$_5$CH$_3$ | |
| 3 | -t-C$_4$H$_9$ | | —CH$_2$CH(CH$_3$)—O—CH(CH$_3$)CH$_2$— | |
| 4 | -t-C$_4$H$_9$ | | —CH$_2$CH$_2$CH(C$_6$H$_5$)CH$_2$CH$_2$— | |
| 5 | -t-C$_4$H$_9$ | —H | —(CH$_2$)$_6$CH$_3$ | |
| 6 | -t-C$_4$H$_9$ | | —CH$_2$CH$_2$CH(—CH$_2$-)$_4$CHCH$_2$— | |
| 7 | -t-C$_4$H$_9$ | —H | —(CH$_2$)$_7$CH$_3$ | |
| 8 | -t-C$_4$H$_9$ | —H | —(CH$_2$)$_4$CH$_3$ | |
| 9 | -t-C$_4$H$_9$ | | —(CH$_2$)$_4$— | |

TABLE I[1,2]-continued $$R^1-\text{cyclohexyl}-\text{spiro}(O)-CH_2-NR^4R^5 \quad I$$

| | $R^1$ | $R^4$ | $R^5$ | ACID |
|---|---|---|---|---|
| 10 | -t-$C_4H_9$ | —($CH_2$)$_5$— | | |
| 11 | -t-$C_4H_9$ | —($CH_2$)$_2$—O—($CH_2$)$_2$— | | |
| 12 | -t-$C_4H_9$ | —($CH_2$)$_3CH_3$ | —($CH_2$)$_3CH_3$ | |
| 13 | -t-$C_4H_9$ | —($CH_2$)$_2CH_3$ | —($CH_2$)$_2CH_3$ | |
| 14 | -t-$C_4H_9$ | —$CH_3$ | —($CH_2$)$_5CH_3$ | |
| 15 | -t-$C_4H_9$ | —$CH_2CH(CH_3)CH_2CH(CH_3)CH_2$— | | |
| 16 | -t-$C_4H_9$ | —H | —$C_6H_{11}$ | |
| 17 | -t-$C_4H_9$ | —CH($CH_3$)(—$CH_2$-)$_4$ | | |
| 18 | -t-$C_4H_9$ | —$CH_2CH(CH_3)(CH_2)_3$— | | |
| 19 | -t-$C_4H_9$ | —($CH_2$)$_2CH(CH_3)(CH_2)_2$— | | |
| 20 | -t-$C_4H_9$ | —$CH_3$ | —$C_6H_{11}$ | |
| 21 | -t-$C_4H_9$ | —($CH_2$)$_6$— | | |
| 22 | -t-$C_4H_9$ | —H | —$C_6H_5$ | |
| 23 | -t-$C_4H_9$ | —H | —$C_6H_4$-4-Cl | |
| 24 | -t-$C_4H_9$ | —H | —$C_6H_4$-4-t-$C_4H_9$ | |
| 25 | -t-$C_4H_9$ | —H | —$C_6H_4$-4-n-$C_4H_9$ | |
| 26 | -t-$C_4H_9$ | —H | —$CH_2$—$C_6H_4$-4-$C_4H_9$ | |
| 27 | -t-$C_4H_9$ | —H | —($CH_2$)$_5CH_3$ | |
| 28 | -t-$C_4H_9$ | —H | —$CH_2$—$C_6H_4$-4-$CH_3$ | |
| 29 | -t-$C_4H_9$ | —H | —$CH_2$—$C_6H_4$-4-Br | |
| 30 | -t-$C_4H_9$ | —H | —$CH_2$—$C_6H_4$-4-F | |
| 31 | -t-$C_4H_9$ | —H | —$CH_2$—$C_6H_5$ | |
| 32 | —H | —H | —($CH_2$)$_5CH_3$ | |
| 33 | —H | —H | —$CH_2$—$C_6H_5$ | |
| 34 | —H | —H | —$CH_2$—$C_6H_4$-4-Cl | |
| 35 | —H | —($CH_2$)$_5$— | | |
| 36 | —H | —$CH_2CH(CH_3)$—O—$CH(CH_3)CH_2$— | | |
| 37 | -t-$C_4H_9$ | —H | —($CH_2$)$_5CH_3$.HCl | |
| 38 | -t-$C_4H_9$ | —H | —($CH_2$)$_5CH_3$.p-toluene-sulphonic acid | |
| 39 | -t-$C_4H_9$ | —H | —($CH_2$)$_5CH_3$.benzoic acid | |
| 40 | -t-$C_4H_9$ | —H | —($CH_2$)$_5CH_3$.saccharate | |
| 41 | -t-$C_4H_9$ | —H | —($CH_2$)$_5CH_3$.acetate | |
| 42 | -t-$C_4H_9$ | —H | —($CH_2$)$_9CH_3$ | |
| 43 | -t-$C_4H_9$ | —H | —($CH_2$)$_{11}CH_3$ | |
| 44 | -t-$C_4H_9$ | —H | —($CH_2$)$_{13}CH_3$ | |
| 45 | -t-$C_4H_9$ | —H | —($CH_2$)$_{15}CH_3$ | |
| 46 | -t-$C_4H_9$ | —H | —($CH_2$)$_{17}CH_3$ | |
| 47 | -t-$C_4H_9$ | —H | —$CH_2$-3-$C_5H_4N$ | |
| 48 | -t-$C_4H_9$ | —($CH_2$)$_3CH_3$ | —$CH_2$-3-$C_5H_4N$ | |
| 49 | -t-$C_5H_{11}$ | —H | —($CH_2$)$_4CH_3$ | |
| 50 | -t-$C_5H_{11}$ | —($CH_2$)$_4CH_3$ | —($CH_2$)$_4CH_3$ | |
| 51 | -t-$C_5H_{11}$ | —H | —$C_6H_{11}$ | |
| 52 | -t-$C_5H_{11}$ | —$CH_2CH(CH_3)CH_2CH(CH_3)CH_2$— | | |
| 53 | -t-$C_5H_{11}$ | —$CH_2CH(CH_3)$—O—$CH(CH_3)CH_2$— | | |
| 54 | —$C_6H_5$ | —H | —($CH_2$)$_4CH_3$ | |
| 55 | —$C_6H_5$ | —($CH_2$)$_3CH_3$ | —($CH_2$)$_3CH_3$ | |
| 56 | —$C_6H_5$ | —H | —$C_6H_{11}$ | |
| 57 | —$C_6H_5$ | —$CH_2CH(CH_3)CH_2CH(CH_3)CH_2$— | | |
| 58 | —$C_6H_5$ | —$CH_2CH(CH_3)$—O—$CH(CH_3)CH_2$— | | |
| 59 | —H | —$CH_3$ | —($CH_2$)$_5CH_3$ | |
| 60 | -t-$C_5H_{11}$ | —$CH_3$ | —($CH_2$)$_5CH_3$ | |
| 61 | —$C_6H_5$ | —$CH_3$ | —($CH_2$)$_5CH_3$ | |
| 62 | -t-$C_4H_9$ | —H | —($CH_2$)$_2CH_3$ | |
| 63 | -t-$C_4H_9$ | —H | —CH($CH_3$)$_2$ | |
| 64 | -t-$C_4H_9$ | —H | —($CH_2$)$_3CH_3$ | |
| 65 | -t-$C_4H_9$ | —H | —CH($CH_3$)($C_2H_5$) | |
| 66 | -t-$C_4H_9$ | —H | —$CH_2CH(CH_3)_2$ | |
| 67 | -t-$C_4H_9$ | —$CH_3$ | —$CH_3$ | |
| 68 | -t-$C_4H_9$ | —$C_2H_5$ | —$C_2H_5$ | |
| 69 | -t-$C_4H_9$ | —($CH_2$)$_5CH_3$ | —($CH_2$)$_5CH_3$ | |
| 70 | -t-$C_4H_9$ | —H | —$C_5H_9$ | |
| 71 | -t-$C_4H_9$ | —H | —$C_3H_5$ | |
| 72 | -t-$C_4H_9$ | —$C_2H_5$ | —($CH_2$)$_4CH_3$ | |
| 73 | -t-$C_4H_9$ | —($CH_2$)$_2CH_3$ | —($CH_2$)$_4CH_3$ | |
| 74 | -t-$C_4H_9$ | —($CH_2$)$_3CH_3$ | —($CH_2$)$_4CH_3$ | |
| 75 | -t-$C_4H_9$ | —$CH_2CH(CH_3)_2$ | —($CH_2$)$_4CH_3$ | |
| 76 | -t-$C_4H_9$ | —CH($CH_3$)$_2$ | —($CH_2$)$_4CH_3$ | |
| 77 | -t-$C_4H_9$ | —$C_6H_{11}$ | —($CH_2$)$_4CH_3$ | |
| 78 | -t-$C_4H_9$ | —$CH_3$ | —($CH_2$)$_4CH_3$ | |
| 79 | -t-$C_4H_9$ | —$CH_2CH$=$CH_2$ | —$C_6H_{11}$ | |

TABLE I[1,2]-continued

|   | R[1] | R[4] | R[5] | ACID |
|---|---|---|---|---|
| 80 | -t-C$_4$H$_9$ | —CH$_3$ | —C$_6$H$_{11}$ | |
| 81 | -t-C$_4$H$_9$ | —H | -t-C$_4$H$_9$ | |
| 82 | -t-C$_4$H$_9$ | —H | —CH$_2$C$_6$H$_{11}$ | |
| 83 | -t-C$_4$H$_9$ | —H | —CH(C$_2$H$_5$)$_2$ | |
| 84 | -t-C$_4$H$_9$ | —H | —(CH$_2$)$_5$CH$_3$ (+ R$^2$ = -2-CH$_3$) | |
| 85 | -t-C$_4$H$_9$ | —H | -2-norbornyl | |
| 86 | -t-C$_4$H$_9$ | —H | -2-adamantyl | |
| 87 | -t-C$_4$H$_9$ | —H | -(2-CH$_3$)—C$_6$H$_{10}$ | |
| 88 | -t-C$_4$H$_9$ | —H | -(3-CH$_3$)—C$_6$H$_{10}$ | |
| 89 | -t-C$_4$H$_9$ | —H | -(4-CH$_3$)—C$_6$H$_{10}$ | |
| 90 | -t-C$_4$H$_9$ | —H | -(4-OH)—C$_6$H$_{10}$ | |
| 91 | -t-C$_4$H$_9$ | —CH$_3$ | —CH$_2$C$_6$H$_{11}$ | |
| 92 | -t-C$_4$H$_9$ | —C$_2$H$_5$ | —CH$_2$C$_6$H$_{11}$ | |
| 93 | -t-C$_4$H$_9$ | —(CH$_2$)$_2$CH$_3$ | —CH$_2$C$_6$H$_{11}$ | |
| 94 | -t-C$_4$H$_9$ | —CH$_3$ | —CH(C$_2$H$_5$)$_2$ | |
| 95 | -t-C$_4$H$_9$ | —C$_2$H$_5$ | —CH(C$_2$H$_5$)$_2$ | |
| 96 | -t-C$_4$H$_9$ | —(CH$_2$)$_2$CH$_3$ | —CH(C$_2$H$_5$)$_2$ | |
| 97 | -t-C$_4$H$_9$ | —H | —H | |
| 98 | -t-C$_4$H$_9$ | —H | —CH(—(CH$_2$)$_2$CH(—(CH$_2$)$_4$—)CHCH$_2$—) | |
| 99 | -t-C$_4$H$_9$ | —H | —CH(n-C$_3$H$_7$)$_2$ | |
| 100 | -t-C$_4$H$_9$ | —H | —(CH$_2$)$_2$C$_6$H$_{11}$ | |
| 101 | -t-C$_4$H$_9$ | —H | —CH(CH$_3$)(CH$_2$)$_4$CH$_3$ | |
| 102 | -t-C$_4$H$_9$ | —H | —CH(C$_2$H$_5$)(CH$_2$)$_3$CH$_3$ | |
| 103 | -t-C$_4$H$_9$ | —CH$_2$CH=CH$_2$ | —CH$_2$CH=CH$_2$ | |
| 104 | -t-C$_4$H$_9$ | —H | —C$_7$H$_{13}$ | |
| 105 | -t-C$_4$H$_9$ | —H | —CH(CH$_3$)(CH$_2$)$_5$CH$_3$ | |
| 106 | -t-C$_4$H$_9$ | —H | —C(CH$_3$)$_2$CH$_2$C(CH$_3$)$_3$ | |
| 107 | -t-C$_4$H$_9$ | —H | —CH(CH$_3$)(CH$_2$)$_3$CH(CH$_3$)$_2$ | |
| 108 | -t-C$_4$H$_9$ | —H | —CH$_2$CH$_2$(1-cyclohexenyl) | |
| 109 | -t-C$_4$H$_9$ | —H | -((4-t-butyl)-C$_6$H$_{10}$) | |
| 110 | -t-C$_4$H$_9$ | —H | —CH(CH$_3$)CH$_2$CH(CH$_3$)$_2$ | |
| 111 | -t-C$_4$H$_9$ | —H | —CH$_2$CH$_2$-t-C$_4$H$_9$ | |
| 112 | -t-C$_4$H$_9$ | —H | —CH(CH$_3$)CH$_2$CH(CH$_3$)C$_2$H$_5$ | |
| 113 | 2,4,6-(CH(CH$_2$-)$_3$) | —CH$_2$CH$_2$CH(—CH$_2$-)$_4$CHCH$_2$— | | |
| 114 | -t-C$_4$H$_9$ | —CH$_2$CH$_2$(1,2-benzylene)CH$_2$— | | |
| 115 | 2,4,6-(CH(CH$_2$-)$_3$) | —H | -n-C$_8$H$_{17}$ | |
| 116 | -t-C$_4$H$_9$ | —CH$_2$CH$_2$CH$_2$CH(—CH$_2$-)$_4$CH— | | |
| 117 | -t-C$_4$H$_9$ | —CH$_3$ | —CH$_2$CH$_2$C$_6$H$_{11}$ | |
| 118 | -t-C$_4$H$_9$ | —C$_2$H$_5$ | —CH$_2$CH$_2$C$_6$H$_{11}$ | |
| 119 | -t-C$_4$H$_9$ | -n-C$_3$H$_7$ | —CH$_2$CH$_2$C$_6$H$_{11}$ | |
| 120 | -t-C$_4$H$_9$ | —H | —CH$_2$C(—CH$_2$-)$_5$CH$_3$ | |
| 121 | -t-C$_4$H$_9$ | —CH$_3$ | —CH$_2$CH(CH$_3$)$_2$ | |
| 122 | -t-C$_4$H$_9$ | -i-C$_3$H$_7$ | —CH$_2$CH$_2$C$_6$H$_{11}$ | |
| 123 | -t-C$_4$H$_9$ | -n-C$_3$H$_7$ | —CH$_2$CH(CH$_3$)$_2$ | |
| 124 | -t-C$_4$H$_9$ | —H | —C(CH$_3$)=CHCOCH$_2$CH(CH$_3$)$_2$ | |
| 125 | -t-C$_4$H$_9$ | —CH$_3$ | —CH$_2$-(1-methylcyclohexyl) | — |
| 126 | -t-C$_4$H$_9$ | —C$_2$H$_5$ | —CH$_2$-(1-methylcyclohexyl) | — |
| 127 | -t-C$_4$H$_9$ | —C$_3$H$_7$ | —CH$_2$-(1-methylcyclohexyl) | — |
| 128 | -t-C$_4$H$_9$ | —CH$_3$ | -2-Norbornyl | — |
| 129 | -t-C$_4$H$_9$ | —C$_2$H$_5$ | -2-Norbornyl | — |
| 130 | -t-C$_4$H$_9$ | —C$_3$H$_7$ | -2-Norbornyl | — |
| 131 | -t-C$_4$H$_9$ | —CH$_3$ | —CH$_2$—C(CH$_3$)$_3$ | — |
| 132 | -t-C$_4$H$_9$ | —C$_2$H$_5$ | —CH$_2$—C(CH$_3$)$_3$ | — |
| 133 | -t-C$_4$H$_9$ | —C$_3$H$_7$ | —CH$_2$—C(CH$_3$)$_3$ | — |
| 134 | -t-C$_4$H$_9$ | —H | —CH$_2$—C(CH$_3$)$_3$ | — |
| 135 | —C(CH$_3$)$_2$—CH$_2$—C(CH$_3$)$_3$ | —(CH$_2$)$_2$CH(CH$_3$)(CH$_2$)$_2$— | | — |
| 136 | —C(CH$_3$)$_2$—CH$_2$—C(CH$_3$)$_3$ | —CH$_2$CH(CH$_3$)CH$_2$CH(CH$_3$)CH$_2$— | | — |
| 137 | —C(CH$_3$)$_2$—CH$_2$—C(CH$_3$)$_3$ | —H | —CH$_2$—CH(CH$_3$)$_2$ | — |
| 138 | -t-C$_4$H$_9$ | —H | -2-Decalyl | HCl |
| 139 | —C(CH$_3$)$_2$C$_6$H$_{11}$ | —H | —CH$_2$—CH(CH$_3$)$_2$ | — |
| 140 | —C(CH$_3$)$_2$C$_6$H$_{11}$ | —CH$_3$ | -n-C$_6$H$_{13}$ | — |
| 141 | —C(CH$_3$)$_2$C$_6$H$_{11}$ | —(CH$_2$)$_2$CH(CH$_3$)(CH$_2$)$_2$— | | — |
| 142 | —C(CH$_3$)$_2$C$_6$H$_{11}$ | —H | —C$_6$H$_{11}$ | — |
| 143 | -t-C$_4$H$_9$ | —CH$_2$—CH(CH$_3$)$_2$ | —CH$_2$—CH(CH$_3$)$_2$ | — |
| 144 | -t-C$_4$H$_9$ | —H | —(CH$_2$)$_2$OCH$_3$ | — |
| 145 | -t-C$_4$H$_9$ | —H | —CH$_2$-(2-THF) | — |

TABLE I[1,2]-continued

| | R[1] | R[4] | R[5] | ACID |
|---|---|---|---|---|
| 146 | -t-C$_4$H$_9$ | —H | —CH$_2$CH(OCH$_3$)$_2$ | — |
| 147 | -t-C$_4$H$_9$ | —(CH$_2$)$_2$OCH$_3$ | —(CH$_2$)$_2$OCH$_3$ | — |
| 148 | -t-C$_4$H$_9$ | —CH$_3$ | —CH$_2$CH(OCH$_3$)$_2$ | — |
| 149 | -t-C$_4$H$_9$ | —CH$_3$ | —CH$_2$-2-(1,3-dioxolanyl) | — |
| 150 | -t-C$_4$H$_9$ | —CH$_3$ | —(CH$_2$)$_2$OCH$_3$ | — |
| 151 | -t-C$_4$H$_9$ | —CH$_3$ | —CH$_2$-(2-THF) | — |
| 152 | -t-C$_4$H$_9$ | —C$_2$H$_5$ | —CH$_2$-(2-THF) | — |
| 153 | -t-C$_4$H$_9$ | —H | —CH$_2$CH(OC$_2$H$_5$)$_2$ | — |
| 154 | -t-C$_4$H$_9$ | —C$_2$H$_5$ | —CH$_2$CH(OCH$_3$)$_2$ | — |
| 155 | -t-C$_4$H$_9$ | —CH$_3$ | —CH$_2$CH(OC$_2$H$_5$)$_2$ | — |
| 156 | -t-C$_4$H$_9$ | —C$_2$H$_5$ | —CH$_2$CH(OC$_2$H$_5$)$_2$ | — |
| 157 | -t-C$_4$H$_9$ | —H | —CH$_2$-(1-methylcyclohexyl) | HCl |
| 158 | -t-C$_4$H$_9$ | —H | —CH$_2$-(1-methylcyclohexyl) | HBr |
| 159 | -t-C$_4$H$_9$ | —H | —CH$_2$-(1-methylcyclohexyl) | H$_3$BO$_3$ |
| 160 | -t-C$_4$H$_9$ | —H | —CH$_2$-(1-methylcyclohexyl) | ½HOOC—COOH |
| 161 | -t-C$_4$H$_9$ | —H | —CH$_2$-(1-methylcyclohexyl) | CH$_3$COOH |
| 162 | -t-C$_4$H$_9$ | —H | —CH$_2$-(1-methylcyclohexyl) | CF$_3$COOH |
| 163 | -t-C$_4$H$_9$ | —H | —CH$_2$-(1-methylcyclohexyl) | C$_3$H$_7$COOH |
| 164 | -t-C$_4$H$_9$ | —H | —CH$_2$-(1-methylcyclohexyl) | C$_5$H$_{11}$COOH |
| 165 | -t-C$_4$H$_9$ | —H | —CH$_2$-(1-methylcyclohexyl) | C$_{11}$H$_{23}$COOH |
| 166 | -t-C$_4$H$_9$ | —H | —CH$_2$-(1-methylcyclohexyl) | C$_{15}$H$_{31}$COOH |
| 167 | -t-C$_4$H$_9$ | —H | —CH$_2$-(1-methylcyclohexyl) | C$_6$H$_5$B(OH)$_2$ |
| 168 | -t-C$_4$H$_9$ | —H | —CH$_2$-(1-methylcyclohexyl) | saccharin |
| 169 | -t-C$_4$H$_9$ | —H | —CH(C$_2$H$_5$)C$_4$H$_9$ | HCl |
| 170 | -t-C$_4$H$_9$ | —H | —CH(C$_2$H$_5$)C$_4$H$_9$ | HBr |
| 171 | -t-C$_4$H$_9$ | —H | —CH(C$_2$H$_5$)C$_4$H$_9$ | H$_3$BO$_3$ |
| 172 | -t-C$_4$H$_9$ | —H | —CH(C$_2$H$_5$)C$_4$H$_9$ | ½HOOC—COOH |
| 173 | -t-C$_4$H$_9$ | —H | —CH(C$_2$H$_5$)C$_4$H$_9$ | CH$_3$COOH |
| 174 | -t-C$_4$H$_9$ | —H | —CH(C$_2$H$_5$)C$_4$H$_9$ | CF$_3$COOH |
| 175 | -t-C$_4$H$_9$ | —H | —CH(C$_2$H$_5$)C$_4$H$_9$ | C$_3$H$_7$COOH |
| 176 | -t-C$_4$H$_9$ | —H | —CH(C$_2$H$_5$)C$_4$H$_9$ | C$_5$H$_{11}$COOH |
| 177 | -t-C$_4$H$_9$ | —H | —CH(C$_2$H$_5$)C$_4$H$_9$ | C$_{11}$H$_{23}$COOH |
| 178 | -t-C$_4$H$_9$ | —H | —CH(C$_2$H$_5$)C$_4$H$_9$ | C$_{15}$H$_{31}$COOH |
| 179 | -t-C$_4$H$_9$ | —H | —CH(C$_2$H$_5$)C$_4$H$_9$ | C$_6$H$_5$B(OH)$_2$ |
| 180 | -t-C$_4$H$_9$ | —H | —CH(C$_2$H$_5$)C$_4$H$_9$ | saccharin |

TABLE Ia[1]

| | R[1] | R[4] | R[5] | ACID |
|---|---|---|---|---|
| 181 | -t-C$_4$H$_9$ | —H | —H | — |
| 182 | -t-C$_4$H$_9$ | —H | —C$_6$H$_{11}$ | — |
| 183 | -t-C$_4$H$_9$ | —H | -n-C$_8$H$_{17}$ | — |
| 184 | -t-C$_4$H$_9$ | —H | -n-C$_6$H$_{13}$ | — |
| 185 | -t-C$_4$H$_9$ | —H | —C$_6$H$_{11}$ | HCl |
| 186 | -t-C$_4$H$_9$ | —CH$_2$—CH(CH$_3$)$_2$ | —CH$_2$—CH(CH$_3$)$_2$ | — |
| 187 | -t-C$_4$H$_9$ | —CH$_3$ | —C$_6$H$_{11}$ | — |
| 188 | -t-C$_4$H$_9$ | —C$_2$H$_5$ | —C$_6$H$_{11}$ | — |

TABLE Ib[1]

| | R[1] | R[4] | R[5] | ACID |
|---|---|---|---|---|
| 189 | -t-C$_4$H$_9$ | —H | —C$_6$H$_{11}$ | — |
| 190 | -t-C$_4$H$_9$ | —H | —H | HCl |
| 191 | -t-C$_4$H$_9$ | —CH$_3$ | —CH$_3$ | — |
| 192 | -t-C$_4$H$_9$ | —H | -(3-methyl)-cyclohexyl | — |
| 193 | -t-C$_4$H$_9$ | —H | —CH(C$_3$H$_7$)C$_3$H$_7$ | HCl |
| 194 | -t-C$_4$H$_9$ | —H | —CH(CH$_3$)C$_5$H$_{11}$ | — |
| 195 | -t-C$_4$H$_9$ | —H | —C$_7$H$_{13}$ | — |
| 196 | -t-C$_4$H$_9$ | —C$_4$H$_9$ | -n-C$_4$H$_9$ | — |
| 197 | -t-C$_4$H$_9$ | —H | —CH(C$_2$H$_5$)C$_4$H$_9$ | — |
| 198 | -t-C$_4$H$_9$ | —H | -2-decalyl | — |
| 199 | -t-C$_4$H$_9$ | —CH$_3$ | —C$_6$H$_{11}$ | — |
| 200 | -t-C$_4$H$_9$ | —C$_2$H$_5$ | —C$_6$H$_{11}$ | — |
| 201 | -t-C$_4$H$_9$ | —CH$_3$ | —CH(CH$_3$)C$_5$H$_{11}$ | — |
| 202 | -t-C$_4$H$_9$ | —C$_2$H$_5$ | —CH(CH$_3$)C$_5$H$_{11}$ | — |
| 203 | -t-C$_4$H$_9$ | —(CH$_2$)$_5$— | | — |
| 204 | -t-C$_4$H$_9$ | —(CH$_2$)$_2$—O—(CH$_2$)$_2$— | | — |
| 205 | -t-C$_4$H$_9$ | —H | -(4-t-butyl)-cyclohexyl | — |
| 206 | -t-C$_4$H$_9$ | —H | -(4-methyl)-cyclohexyl | — |
| 207 | -t-C$_4$H$_9$ | —H | -(2-methyl)-cyclohexyl | — |
| 208 | -t-C$_4$H$_9$ | —H | —C$_5$H$_9$ | — |

TABLE Ib[1]-continued

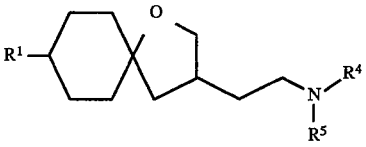

| | R[1] | R[4] | R[5] | ACID |
|---|---|---|---|---|
| 209 | -t-C$_4$H$_9$ | —H | —(CH$_2$)-2-THF | — |
| 210 | -t-C$_4$H$_9$ | —CH$_3$ | —CH(C$_2$H$_5$)C$_4$H$_9$ | — |
| 211 | -t-C$_4$H$_9$ | —C$_2$H$_5$ | —CH(C$_2$H$_5$)C$_4$H$_9$ | — |
| 212 | -t-C$_4$H$_9$ | —C$_3$H$_7$ | —CH(C$_2$H$_5$)C$_4$H$_9$ | — |

THF means tetrahydrofurfuryl, acid means that the compound is a ammonium salt of the denoted acid

[1]C$_6$H$_5$ means phenyl, C$_7$H$_{13}$ means cycloheptyl, C$_6$H$_{11}$ means cyclohexyl, C$_5$H$_9$ means cyclopentyl, C$_3$H$_5$ means cyclopropyl, C$_5$H$_4$N means pyridyl, C$_6$H$_{10}$ means cyclohexylene.

[2]All substituents R[1] are at the four position of the cyclohexyl ring except compounds 113 and 115 which are derived from adamantanone.

Physical data for the above compounds are set out in Tables II, III, IV and V.

TABLE II

| Compound No. | Melting Point (°C.) |
|---|---|
| 1 | 50–60 |
| 4 | 115–115 |
| 6 | 72–75 |
| 9 | 68–75 |
| 10 | 82–87 |
| 11 | 72–77 |
| 15 | 48–60 |
| 19 | 50–60 |
| 21 | 60–63 |
| 22 | 135 |
| 23 | 122–125 |
| 24 | 140 |
| 25 | 115 |
| 26 | 48–52 |
| 28 | 40–42 |
| 29 | 50–52 |
| 37 | 250 (dec.) |
| 38 | 190–200 |
| 40 | 105–115 |
| 50 | 85–90 (HCl salt) |
| 51 | 270–275 (HCl salt) |
| 52 | 44–47 |
| 53 | 61–65 |
| 56 | 47–57 |
| 56 | 226–234 (HCl salt) |
| 57 | 261–273 (HCl salt) |
| 58 | 253–262 (HCl salt) |
| 97 | 80–92 |
| 109 | 76–80 |
| 111 | 56–60 |
| 114 | 75–76 |
| 128 | 60–65 |
| 138 | 249–53 |
| 141 | 91–97 |
| 143 | 42–44 |
| 157 | 248–55 Dec. |
| 158 | 254–56 Dec. |
| 160 | 210–212 |
| 162 | 195–96 Dec. |
| 168 | 216–20 Dec. |
| 172 | 156–58 |
| 185 | 243–46 Dec. |
| 190 | 260–65 |

TABLE III

| Compound No. | Refraction Index ($n_D^{22}$) |
|---|---|
| 2 | 1.4750 |
| 5 | 1.4765 |
| 7 | 1.4748 |
| 8 | 1.4752 |
| 12 | 1.4749 |
| 13 | 1.4748 |
| 14 | 1.4744 |
| 16 | 1.4928 |
| 17 | 1.4938 |
| 18 | 1.4889 |
| 20 | 1.4942 |
| 27 | 1.4752 |
| 30 | 1.5105 |
| 31 | 1.5191 |
| 32 | 1.4740 |
| 33 | 1.5326 |
| 34 | 1.5389 |
| 35 | 1.4971 |
| 36 | 1.4883 |
| 39 | 1.5140 |
| 42 | 1.4748 |
| 43 | 1.4750 |
| 44 | 1.4745 |
| 45 | 1.4742 |
| 46 | 1.4748 |
| 47 | 1.5202 |
| 48 | 1.5086 |
| 49 | 1.4877 |
| 54 | 1.5201 |
| 55 | 1.5120 |
| 59 | 1.4734 |
| 60 | 1.4769 |
| 61 | 1.5148 |
| 62 | 1.4759 |
| 64 | 1.4758 |
| 65 | 1.4760 |
| 66 | 1.4739 |
| 67 | 1.4770 |
| 68 | 1.4780 |
| 69 | 1.4732 |
| 70 | 1.4872 |
| 71 | 1.4870 |
| 72 | 1.4757 |
| 73 | 1.4731 |
| 74 | 1.4729 |
| 75 | 1.4680 |
| 76 | 1.4736 |
| 77 | 1.4865 |
| 78 | 1.4755 |
| 79 | 1.4966 |
| 80 | 1.4945 |
| 81 | 1.4735 |
| 82 | 1.4922 |
| 83 | 1.4763 |
| 84 | 1.4735 |
| 85 | 1.5034 |
| 87 | 1.4894 |
| 89 | 1.4898 |
| 91 | 1.4909 |
| 92 | 1.4900 |
| 93 | 1.4899 |
| 94 | 1.4739 |
| 95 | 1.4740 |
| 96 | 1.4748 |
| 97 | 1.4840 |
| 99 | 1.4726 |
| 101 | 1.4737 |
| 102 | 1.4735 |
| 103 | 1.4879 |
| 104 | 1.4955 |
| 105 | 1.4733 |
| 106 | 1.4761 |
| 107 | 1.4724 |
| 108 | 1.4994 |
| 110 | 1.4766 |
| 113 | 1.5248 (24° C.) |
| 115 | 1.5023 (24° C.) |

TABLE III-continued

| Compound No. | Refraction Index ($n_D^{22}$) |
|---|---|
| 116 | 1.5072 |
| 117 | 1.4898 |
| 118 | 1.4910 |
| 119 | 1.4868 |
| 120 | 1.4902 |
| 121 | 1.4731 |
| 122 | 1.4890 |
| 123 | 1.4720 |
| 125 | 1.4921 |
| 126 | 1.4939 |
| 127 | 1.4906 |
| 129 | 1.4996 |
| 131 | 1.4750 |
| 132 | 1.4754 |
| 133 | 1.4734 |
| 136 | 1.4874 (24° C.) |
| 137 | 1.4797 (24° C.) |
| 139 | 1.4958 (25° C.) |
| 140 | 1.4929 (25° C.) |
| 142 | 1.5002 (25° C.) |
| 144 | 1.4759 |
| 145 | 1.4881 |
| 146 | 1.4745 |
| 147 | 1.4769 |
| 148 | 1.4733 |
| 149 | 1.4850 |
| 150 | 1.4752 |
| 151 | 1.4856 |
| 152 | 1.4888 |
| 153 | 1.4673 |
| 154 | 1.4739 |
| 155 | 1.4665 |
| 156 | 1.4699 |
| 181 | 1.4817 |
| 183 | 1.4840 |
| 184 | 1.4843 |
| 186 | 1.4707 |
| 187 | 1.4900 |
| 188 | 1.4915 |
| 191 | 1.4714 |
| 192 | 1.4862 |
| 193 | 1.4721 |
| 196 | 1.4700 |
| 197 | 1.4722 |
| 198 | 1.5023 |
| 199 | 1.4891 |
| 200 | 1.4913 |
| 201 | 1.4717 |
| 202 | 1.4720 |

TABLE IV

Elemental Analysis

| Compound No. | C Calc. | Found | H Calc. | Found | N Calc. | Found |
|---|---|---|---|---|---|---|
| 41 | 70.93 | 69.26 | 11.62 | 11.93 | 3.93 | 4.80 |
| 63 | 75.80 | 75.24 | 12.33 | 11.91 | 5.52 | 6.60 |
| 100 | 78.44 | 75.66 | 12.22 | 12.10 | 4.35 | 4.63 |
| 112 | 77.60 | 74.41 | 12.70 | 11.90 | 4.52 | 5.29 |

TABLE V

Molecular weight (determined by mass spectrometry)

| Compound No. | Calc. | Found |
|---|---|---|
| 3 | 309 | 309 |
| 86 | 345 | 345 |
| 88 | 307 | 307 |

TABLE V-continued

Molecular weight (determined by mass spectrometry)

| Compound No. | Calc. | Found |
|---|---|---|
| 124 | 335 | 335 |
| 203 | 307 | 307 |
| 204 | 321 | 321 |
| 205 | 378 | 378 |
| 206 | 335 | 335 |
| 207 | 335 | 335 |
| 208 | 307 | 307 |
| 209 | 323 | 323 |
| 210 | 351 | 351 |
| 211 | 365 | 365 |
| 212 | 379 | 379 |

EXAMPLE 182 (COMPOUND 182)

8-t-Butyl-3-cyclohexylaminomethyl-1-oxaspiro(4,5) decane (i) Preparation of 8-t-butyl-3-hydroxy-1-oxaspiro(4,5) decane To an ice cooled solution of 8-t-butyl-1-oxaspiro(4,5) decane-3-one (44.1 g, 0.21 mmol) in methanol (300 ml) was added sodium borohydride (10.8 g, 0.285 mol) in portions. After the evolution of hydrogen ceased the cooling bath was removed and the mixture was stirred at room temperature over night. The solvent was evaporated in vacuo and the residue was taken up in toluene/diluted hydrochloric acid. The organic layer was washed twice with water (200 ml), dried ($MgSO_4$) and evaporated in vacuo to yield a colourless oil (44 g) which was recrystallised from light petroleum. 30 g of colourless crystals were obtained which melted at 82°–84° C. TLC and NMR-analysis indicated a single diastereoisomer only (cis).

(ii) Preparaton of 8-t-butyl-3-(p-toluenesulfonyloxy)-1-oxaspiro-(4,5)decane

To a solution of 8-t-butyl-3-hydroxy-1-oxaspiro(4,5) decane (4.24 g, 20 mmol) in THF (50 ml) was added sodium hydride (0.72 g, 24 mmol, 80% in mineral oil) and the mixture was heated to reflux for 3 hours. p-Toluenesulfonylchloride (4.56 g, 24 mmol) in THF (10 ml) was then added and heating was continued for another 3 hours. The solvent was evaporated, toluene and water were added (50 ml, each) and the phases were separated. A pale yellow oil (7.3 g) was isolated from the organic layer which was treated with light petroleum to yield colourless crystals (5.6 g), melting at 101° C.

(iii) Preparation of 8-t-butyl-3-cyano-1-oxaspiro(4,5) decane

A mixture of 8-t-butyl-3-(p-toluenesulfonyloxy)-1-oxaspiro-(4,5)decane (18.3 g, 50 mmol) and sodium cyanide (4.9 g, 100 mmol) in dry DMF (75 ml) was heated to 100° C. for 6 hours. Light petroleum/ethylacetate 4:1 (50 ml) was added and the mixture was filtrated from insoluble material. The filtrate was then evaporated in vacuo and the resulting residue was taken up in toluene (100 ml). It was washed with water, dried ($MgSO_4$) and evaporated in vacuo to yield a brownish oil (11.0 g) which was Kugelrohr distilled (120°–125° C., 0.015 mbar) to furnish the product as colourless crystals (8.94 g, m.p. 35°–40° C.).

COMPOUND 181

(iv) Preparation of 8-t-butyl-3-aminomethyl-1-oxaspiro (4,5)decane

To a solution of lithium aluminum hydride (LAH) (2.19 g, 58 mmol) in THF (100 ml) was added 8-t-butyl-3-cyano-1-oxaspiro-(4,5)decane (8.5 g, 38.5 mmol) in THF (25 ml). The reaction mixture was refluxed for 3 hours. After cooling excess LAH was carefully destroyed by addition of saturated, aqueous sodium sulfate solution. The reaction mixture was filtrated from insoluble material and the filtrate was evaporated in vacuo. The pale yellow oil (8.6 g) was purified by Kugelrohr distillation (125°–135° C., 0.05 mbar) to yield the product as a colourless liquid (5.7 g, $n_D^{22}$: 1.4817).

(v) Preparation of 8-t-butyl-3-cyclohexylaminomethyl-1-oxaspiro-(4,5)decane

To a solution of 8-t-butyl-3-aminomethyl-1-oxaspiro(4, 5)- decane (1.2 g, 5.3 mmol), cyclohexanone (0.54 g, 5.5 mmol) and zinc chloride (0.4 g, 3 mmol) in methanol (15 ml) was added sodium cyanoborohydride (0.4 g, 6.4 mmol). The reacton mixture was stirred over night. The solvent was then evaporated in vacuo and the resulting residue was treated with a mixture of saturated aqueous sodium carbonate/toluene (50 ml each). The organic layer was separated, dried (MgSO$_4$) and evaporated in vacuo to yield 1.7 g of a pale yellow oil which was purified by flash chromatography (toluene/ethanol 4:1). Evaporaton of the fractions containing the product yielded a colourless oil (1.5 g).

1H-NMR(CDCl$_3$/ppm): 3.93 (dd, 1H); 3.45 (dd, 1H); 2.59 (t,2H); 2.37(m, 1H); 1.88-087(m,22H); 0.82 (s,9H).

EXAMPLES 183–188

By processes similar to those described in Example 182, compounds 127 (8-t-butyl-3-n-octylaminomethyl-1-oxaspiro(4,5)-decane; $n_D^{22}$ 1.4840) and 128 (8-t-butyl-3-n-hexylaminomethyl-1-oxaspiro(4,5)decane; $n_D^{22}$ 1.4843) were prepared.

EXAMPLE 181

8-t-Butyl-3-aminomethyl-1-oxaspiro(4,5)decane

This compound is prepared according to the steps (i) to (iv) of Example 182.

EXAMPLE 189 (COMPOUND 190)

8-t-Butyl-3-cyclohexylaminoethyl-1-oxaspiro(4,5) decane (i) Preparation of 8-t-butyl-3-aminoethyl-1-oxaspiro(4,5) decane hydrochloride To a mixture of cyanoacetic acid (10.2 g, 0.12 mol) and pyridine (50 ml) was added piperidine (0.85 g, 0.01 mol) and 8-t-butyl-1-oxaspiro(4,5)decane-3-one. The mixture was heated to reflux until the evolution of carbon dioxide ceased (4 hours). The solvent was then evaporated in vacuo and toluene (50 ml) was added and distilled off two times. The resulting yellow oil (24 g) was filtrated over a plug of silica (toluene/5% ethylacetate) to remove polar side products. Evaporation of the organic washings resulted in a pale yellow oil (19.4 g) which was transferred to the hydrogenation step without further purification.

The above product was dissolved in methanol (200 ml). Concentrated hydrochloric acid (8.2 ml) and platinum oxide was added and the mixture was hydrogenated (60° C., 5 bar) until hydrogen uptake ceased. The solvent was then evaporated in vacuo and toluene (100 ml) was added/distilled off the residue two times. The resulting residue was then treated with light petroleum (150 ml). Colourless crystals (8.7 g) were isolated by filtration (m.p. 260°–65° C.).

(ii)Preparation of 8-t-butyl-3-cyclohexylaminoethyl-1-oxaspiro-(4,5)decane)

To a solution of 8-t-butyl-3-aminoethyl-1-oxaspiro(4,5) decane hydrochloride (1.10 g, 4 mmol) in methanol (15 ml) was added sodium methylate (4 ml, 1N in methanol), cyclohexanone (0.41 g, 4.2 mmol) zinc chloride (0.32 g, 2.5 mmol) and sodium cyanoborohydride (0.32 g, 5 mmol). The reaction mixture was stirred at room temperature over night. The solvent was removed in vacuo and the residue was taken up in toluene (50 ml)/sat. aqueous sodium carbonate (50 ml). Drying and evaporation of the organic layer furnished the product as a colurless oil (1.3 g). It was purified by flash chromatography (light petroleum/triethylamine 10:1). Evaporation of the fractions containing the product furnished a colourless oil (1.0 g). 1H-NMR (CDCl$_3$, ppm): 3.93 (t,1H); 3.37(t,1H); 2.58(m,2H); 2.37(m, 1H); 2.27(m, 1H); 1.93-0.90(m,24H); 0.85(s,9H).

EXAMPLE 213

8-t-Butyl-3-cyclohexylaminomethyl-3-hydroxy-1-oxaspiro(4,5)decane (i) Preparation of 8-t-butyl-3-hydroxy-3-cyano-1-oxaspiro-4,5)decane To a solution of 8-t-butyl-1-oxaspiro(4,5)decane-3-one (2.1 g, 10 mmol) in ethanol (20 ml) was added finely powdered sodium cyanide (0.73 g, 15 mmol) with stirring. Acetic acid (1.2 g, 20 mmol) was then added and the reaction mixture was stirred at room temperature overnight. The solvent was then evaporated in vacuo, toluene (50 ml) was added to the residue and the mixture was filtrated. Evaporation of the filtrate in vacuo resulted in a residue which was recrystallized from light petroleum to yield a colourless powder (1.25 g, m.p. 114°–116° C.). TLC and NMR analysis indicated the compound being a single diastereoisomer (cis).

(ii) Preparation of 8-t-butyl-3-aminomethyl-3-hydroxy-1-oxaspiro(4,5)decane 8-t-Butyl-3-hydroxy-3-cyano-1-oxaspiro(4,5)decane (2.37 g, 10 mmol) in methanol (25 ml), containing conc. hydrochloric acid (1 ml), was hydrogenated on platinum oxide (0.1 g, 40° C./5 bar hydrogen pressure) until the uptake of hydrogen ceased. Saturated NaHCO$_3$ (3 ml) was added and the solvent was evaporated in vacuo. To the residue was added methanol (30 ml) and MgSO$_4$. The mixture was filtrated and the filtrate was evaporated in vacuo to yield a pale greenish solid (2.0 g). The fairly polar compound was not further purified. It was characterised via its N-cyclohexyl derivative.

(iii) Preparation of 8-t-butyl-3-cyclohexylaminomethyl-3-hydroxyl-1-oxaspiro(4,5)decane To a solution of 8-t-butyl-3-aminomethyl-3-hydroxy-1-oxaspiro-(4,5)decane (1.8 g, 7.5 mmol), cyclohexanone (1.36 g, 8 mmol) and zinc chloride (0.61 g, 4.5 mmol) in methanol (20 ml) was added sodium cyanoborohydride (0.56 g, 9 mmol). The reaction mixture was stirred at room temperature overnight. The solvent was then evaporated in vacuo and to the resulting residue was added saturated sodium carbonate solution and toluene (50 ml each). The organic layer was separated, dried (MgSO$_4$) and evaporated in vacuo to yield a semisolid residue (2.0 g) which was treated with light petroleum. A colourless powder was isolated by filtration (1.0 g) which melted at 113°–115° C.

EXAMPLE 214 (COMPOUND 99)

3-Hept-4-ylamino-8-t-butyl-1-oxaspiro(4,5)-decane (compound 99)

(i) Preparation of 8-t-butyl-1-oxaspiro(4,5)decane-3-one oxime

To a solution of hydroxylamine hydrochloride (6.9 g, 0.1 mol) and triethylamine (10.0 g, 0.1 mol) in 10 ml of water was added 8-t-butyl-1-oxaspiro(4,5)decane-3-one (16.0 g, 0.076 mol) in 30 ml tetrahydrofuran. The mixture was stirred at room temperature for 3 hours and at 60° C. for 1 hour. The solvent was then evaporated in vacuo and the residue was partitioned between toluene and brine (100 ml each). The organic layer was washed with brine, dried (MgSO$_4$) and evaporated in vacuo to yield a colourless oil (17.0 g) which crystallised on standing. Recrystallisation from light petroleum gave two fractions of colourless crystals (6.6 g and 5.3 g) mp.: 118–120 and 105°–108° C. $^1$H-NMR indicated mixtures of geometric isomers (E/Z) in ratios of 1:1 and 2:1 respectively.

(ii) Preparation of 3-amino-8-t-butyl-1-oxaspiro(4,5)-decane 8-t-Butyl-1-oxaspiro(4,5)-decane-3-one oxime (17.5 g, 76 mmol) in tetrahydrofuran (50 ml) was added to a solution of lithium- aluminium hydride (4.5 g, 0.125 mol) in tetrahydrofuran (100 ml). The reaction mixture was refluxed for 4 hours, cooled end excess LAH was hydrolysed by addition of saturated aqueous sodium sulfate solids were filtered off washed with tetrahydrofuran and the solvent was stripped off in vacuo. Kugelrohr distillation of the resulting pale yellow oil (16.9 g) gave a colourless oil (12.3 g). Bp.: 125° C./0.02 mbar, $n_D^{22}$:1.4840.

(iii) Preparation of 3-hept-4-ylamino-8-t-butyl-1-oxaspiro (4,5)-decane)

To 3-amino-8-t-butyl-1-oxaspiro(4,5)-decane (1.12 g, 5 mmol) and heptane-4-one (0.6 g, 5.25 mmol) in dry methanol (20 ml) was added zinc chloride (0.41 g, 3 mmol). The mixture was stirred at room temperature for 5 minutes and sodium cyanoborohydride 0.38 g, 6 mmol) was added and the resulting heterogeneous mixture was stirred at room temperature overnight. The solvent was then stripped off in vacuo, toluene (50 ml) and 2N NaOH (50 ml) was added. The aqueous phase was extracted twice with toluene (2×50 ml) and the combined organic layers were dried (MgSO$_4$) and concentrated in vacuo. The resulting oil was purified by flash chromatography to give a pale yellow oil (1.12 g). $n_D$:1.4726.

Fungicidal Activity

The fungicidal activity of compounds of the invention was investigated by means of the following tests.

(a) Antisporulant activity against vine downy mildew (*Plasmopara viticola*; PVA)

The test is a direct antisporulant one using a foliar spray. The lower surfaces of leaves of whole vine plants (cv Cabernet Sauvignon), approximately 8 cm high, are inoculated by spraying with an aqueous suspension containing 5×10$^4$ zoosporangia/ml. The inoculated plants are kept for 24 hours at 21° C. in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). Plants are treated using an automated sprayline with an atomising nozzle. The concentration of the compound is 600 ppm, and the spray volume is 750 l/ha. After spraying, the plants are returned to normal glasshouse conditions for 96 hours and are then transferred to the high humidity compartment for 24 hours to induce sporulation. Assessment is based on the percentage of the leaf area covered by sporulation compared with that on control leaves.

b) Activity against tomato early blight (*Alternaria solani*; AS)

This test measures the contact prophylactic activity of test compounds applied as a foliar spray. Tomato seedlings (cv Outdoor Girl) are grown to the stage at which the second true leaf is expanded. The plants are treated using an automated sprayline as described under (a). Test compounds are applied as solutions or suspensions in a mixture of acetone and water (50:50 v/v) containing 0.04% surfactant ("TWEEN 20"—Trade Mark). After drying the plants are kept for 24 hours in a glasshouse at 20° C. and 40% R.H., followed by inoculaton of the leaf upper surfaces with a suspension of *A. solani* conidia containing 10$^4$ spores/mi. For 4 days after inoculation plants are kept moist in a humidity compartment at 21° C. Disease is assessed 4 days after inoculation, based on the percentage of leaf surface area covered by lesions when compared with control plants.

(c) Direct protectant activity against broad bean grey mould (*Botrytis cinerea*; BCB)

The test is a direct protectant foliar spray. The upper surfaces of leaves of broad bean plants with two leaf pairs (cv The Sutton) are sprayed with the test compound at a dosage of 600 ppm using an automated sprayline as described under (a). 24 hours after spraying the leaves are inoculated with an aqueous suspension containing 10$^6$ conidia/ml. For 4 days after inoculation plants are kept in a high humidity compartment at 22° C. Disease is assessed 4 days after inoculation, based on the percentage of leaf surface area covered by lesions.

(d) Activity against wheat leafspot (*Leptosphaeria nodorum*; LN.)

The test is a direct therapeutic foliar spray. Leaves of wheat plants (cv Norman), at the single leaf stage, are inoculated by spraying with an aqueous suspension containing 1.5×10$^6$ conidia/ml. The inoculated plants are kept for 24 hours in a high humidity compartment prior to treatment. The plants are sprayed with a solution of the test compound at a dosage of 600 ppm using an automated sprayline as described under (a). After drying, the plants are kept for 6–8 days at 22° C. and moderate humidity (70%). Assessment is based on the density of lesions per leaf compared with that on leaves of control plants.

(e) Activity against barley powdery mildew (*Erysiphe graminis* f.sp. hordei; EGT)

The test is a direct therapeutic foliar spray. Leaves of barley seedlings, (cv. Golden Promise) at the single leaf stage are inoculated by dusting with mildew conidia one day prior to treatment with the test compound. The inoculated plants are kept overnight at glasshouse ambient temperature (18° C.) and humidity (40%) prior to treatment. The plants are sprayed with the test compound at a dosage of 600 ppm using an automated sprayline as described under (a). After drying, plants are returned to a compartment at 18° C. and 40% humidity for up to 7 days. Assessment is based on the percentage of leaf area covered by sporulation compared with that on leaves of control plants.

(f) Direct protectant activity against barley powdery mildew (*Erysiphe graminis* f.sp. hordei; EGP)

The test is a direct protectant foliar spray. Leaves of barley seedlings (cv Golden Promise) at the single leaf stage are sprayed with the test compound as described under (a). After drying, the plants are kept for 24 hours in a glasshouse at 18° C. and 40% R.H. Then the plants are inoculated by dusting with mildew conidia and kept at 18° C. and 40% R.H. for 8 days. Assessment is based on the percentage of leaf area covered by sporulation compared with that on leaves of control plants.

(g) Direct protectant activity against tomato late blight Phytophthora infestants: PIP)

The test is a direct protectant foliar spray. Tomato plants with two expanded leaves (cv First in the Field) are sprayed with the test compound as described under (a). After drying, the plants are kept for 24 hours in the glasshouse at 20° C. and 40% R.H. Then, the upper surfaces of the leaves are inoculated with an aqueous suspension containing $2 \times 10^5$ zoosporangia/ml. The inoculated plants are kept for 24 hours at 18° C. in a high humidity cabinet and 5 days at 15° C. and 80% R.H. in a growth chamber with 14 hours light/day. The assessment is based on the percentage of diseased leaf area compared with that on control leaves.

(h) Activity against wheat eyespot in-vitro (*Pseudocercosporella herpotrichoides*; PHI)

This test measures the in vitro activity of compounds against the fungus causing wheat eyespot. The test compound is dissolved or suspended in acetone and is added into 4 ml aliquots of half strength Potato Dextrose Broth (PDB) dispended in 25-compartment petri dishes to give a final concentration of 10 ppm. The fungal inoculum consists of mycelial fragments of *P. herpotrichoides* grown in half strength PDB in shaken flasks and added to the broth to provide $5 \times 10^4$ fragments/ml broth. Petri dishes are incubated at 20° C. for 10 days until the assessment of mycelial growth.

(i) Activity against Rhizoctonia in-vitro (*Rhizoctonia solani*: RSI)

This test measures the in-vitro activity of compounds against *R. solani* that causes stem and root rots. The test compound in acetone is added into 4 ml aliquots of half strength Potato Dextrose Broth dispensed in 25-compartment petri dishes to give final concentratons of 10 ppm. The fungal inoculum consists of mycelial fragments of *R. solani* growth in half strength PDB in shaken culture flasks and added to the broth to provide $5 \times 10^4$ fragments/ml broth. Petri dishes are incubated at 20° C. for 10 days until the assessment of mycelial growth.

(j) Activity against apple scab in-vitro (*Venturia inaequalis*: VII)

This test measures the in-vitro activity of compounds against *V. inaequalis* that causes apple scab. The test compound in acetone is added into 4 ml aliquots of half strength Potato Dextrose Broth dispensed in 25-compartment petri dishes to give final concentrations of 10 ppm. The fungal inoculum consists of mycelial fragments and spores of *V. inaequalis* grown on malt agar and added to the broth to provide $5 \times 10^4$ propagules/ml broth. Petri dishes are incubated at 20° C. for 10 days until the assessment of mycelial growth.

(k) Activity against rice leaf blast (*Pyricularia oryzae*; PO)

The test is a direct therapeutic foliar spray. The leaves of rice seedlings (cv Aichiaishi—about 30 seedlings per pot) at the stage of the second leaf beginning to bend are sprayed with an aqueous suspension containing 105 spores/ml 24 hours prior to treatment with the test compound. The inoculated plants are kept overnight in high humidity and then allowed to dry before spraying with the test compound at a dosage of 600 ppm using an automated sprayline as described under (a). After treatment the plants are kept in a rice compartment at 25°–30° C. and high humidity. Assessments are made 4–5 days after treatment and are based on the density of necrotic lesions per leaf when compared with control plants.

The extent of disease control in all the above tests is expressed as a rating compared with either an untreated control or a diluent-sprayed-control, according to the criteria:

0=less than 50% disease control
1=about 50–80% disease control
2=greater than 80% disease control The results of the tests are set out in Table VI below.

TABLE VI

| Comp. | PVA | AS | BCB | LN | EGT | EGP | PIP | PHI | RSI | VII | PO |
|---|---|---|---|---|---|---|---|---|---|---|---|
| 1 | 0 | 0 | 0 | 0 | 2 | — | 0 | 1 | 0 | 0 | 0 |
| 2 | 0 | 0 | 0 | 0 | 2 | — | 0 | 1 | 1 | 0 | 0 |
| 3 | 0 | 0 | 0 | 0 | 1 | — | 0 | 2 | 0 | 2 | 0 |
| 4 | 0 | 0 | 0 | 1 | 2 | 2 | 0 | 1 | 0 | 1 | 0 |
| 5 | 0 | 0 | 1 | 0 | 2 | 2 | 0 | 0 | 1 | 0 | 0 |
| 6 | 0 | 0 | 1 | 0 | 2 | 2 | 0 | 0 | 1 | 1 | 0 |
| 7 | 0 | 0 | 1 | 0 | 2 | 2 | 0 | 2 | 2 | 2 | 0 |
| 8 | 0 | 0 | 1 | 0 | 2 | 2 | 0 | 1 | 0 | 1 | 0 |
| 9 | 0 | 0 | 0 | 1 | 2 | 2 | 0 | 1 | 0 | 1 | 0 |
| 10 | 0 | 0 | 2 | 1 | 2 | 2 | 0 | 1 | 0 | 1 | 0 |
| 11 | 0 | 0 | 0 | 0 | 0 | 2 | 0 | 1 | 0 | 1 | 0 |
| 12 | 0 | 0 | 2 | 0 | 2 | 2 | 0 | 0 | 0 | 2 | 0 |
| 13 | 0 | 0 | 0 | 0 | 2 | 2 | 0 | 0 | 0 | 2 | 0 |
| 14 | 0 | 0 | 0 | 1 | 2 | 2 | 0 | 2 | 1 | 2 | 0 |
| 15 | 0 | 0 | 0 | 0 | 2 | 2 | 0 | 0 | 0 | 2 | 0 |
| 16 | 0 | 2 | 1 | 1 | 2 | 2 | 0 | 0 | 0 | 2 | 0 |
| 17 | 0 | 0 | 0 | 0 | 2 | 2 | 0 | 0 | 0 | 0 | 0 |
| 18 | 0 | 0 | 0 | 1 | 2 | 2 | 0 | 0 | 0 | 1 | 0 |
| 19 | 0 | 0 | 0 | 1 | 2 | 2 | 0 | 0 | 0 | 1 | 0 |
| 20 | 0 | 0 | 0 | 0 | 2 | 2 | 0 | 0 | 0 | 1 | 0 |
| 21 | 0 | 0 | 2 | 0 | 2 | 2 | 0 | 0 | 0 | 1 | 0 |
| 22 | 0 | 0 | 0 | 0 | 1 | 1 | 0 | 0 | 0 | 0 | 0 |

TABLE VI-continued

| Comp. | PVA | AS | BCB | LN | EGT | EGP | PIP | PHI | RSI | VII | PO |
|---|---|---|---|---|---|---|---|---|---|---|---|
| 23 | 0 | 0 | 0 | 0 | 0 | 0 | 0 | 0 | 0 | 2 | 0 |
| 24 | 0 | 0 | 0 | 0 | 0 | 0 | 0 | 0 | 0 | 0 | 0 |
| 25 | 0 | 0 | 0 | 0 | 0 | 0 | 0 | 0 | 0 | 0 | 0 |
| 26 | 0 | 1 | 0 | 0 | 2 | 2 | 0 | 1 | 0 | 1 | 0 |
| 27 | 0 | 0 | 0 | 0 | 2 | 2 | 0 | 1 | 0 | 1 | 0 |
| 28 | 0 | 0 | 0 | 0 | 2 | 2 | 0 | 0 | 0 | 2 | 0 |
| 29 | 0 | 0 | 0 | 0 | 2 | 2 | 0 | 0 | 0 | 2 | 0 |
| 30 | 0 | 0 | 0 | 0 | 2 | 2 | 0 | 0 | 0 | 2 | 0 |
| 31 | 2 | 1 | 0 | 0 | 2 | 2 | 0 | 0 | 0 | 1 | 0 |
| 32 | 0 | 0 | 0 | 0 | 2 | 2 | 0 | 0 | 0 | 0 | 0 |
| 33 | 0 | 0 | 0 | 0 | 1 | 0 | 0 | 0 | 0 | 0 | 0 |
| 34 | 0 | 0 | 0 | 0 | 2 | 2 | 0 | 0 | 0 | 0 | 0 |
| 35 | 0 | 0 | 0 | 0 | 0 | 0 | 0 | 0 | 0 | 0 | 0 |
| 36 | 0 | 0 | 0 | 0 | 2 | 2 | 0 | 0 | 0 | 1 | 0 |
| 37 | 0 | 0 | 1 | 0 | 2 | 2 | 0 | 1 | 0 | 0 | 0 |
| 38 | 0 | 2 | 0 | 0 | 2 | 2 | 0 | 2 | 1 | 0 | 0 |
| 39 | 0 | 2 | 0 | 0 | 2 | 2 | 0 | 1 | 0 | 0 | 0 |
| 40 | 0 | 2 | 0 | 0 | 2 | 2 | 0 | 1 | 0 | 0 | 0 |
| 41 | 0 | 0 | 0 | 1 | 2 | 2 | 0 | 1 | 0 | 0 | 0 |
| 42 | 0 | 0 | 0 | 0 | 2 | 2 | 0 | 1 | 0 | 2 | 0 |
| 43 | 0 | 0 | 0 | 2 | 2 | 2 | 0 | 0 | 0 | 2 | 0 |
| 44 | 0 | 0 | 0 | 0 | 2 | 2 | 0 | 0 | 0 | 0 | 0 |
| 45 | 0 | 0 | 0 | 0 | 2 | 2 | 0 | 0 | 0 | 0 | 0 |
| 46 | 0 | 0 | 0 | 0 | 2 | 2 | 0 | 0 | 0 | 0 | 0 |
| 47 | 0 | 2 | 0 | 0 | 2 | 2 | 0 | 0 | 0 | 1 | 0 |
| 48 | 0 | 2 | 0 | 0 | 2 | 2 | 0 | 0 | 0 | 1 | 0 |
| 49 | 0 | 0 | 0 | 2 | 2 | 2 | 2 | 2 | 1 | 1 | 0 |
| 50 | 0 | 0 | 0 | 0 | 2 | 2 | 0 | 0 | 0 | 1 | 0 |
| 51 | 0 | 2 | 0 | 0 | 2 | 2 | 2 | 1 | 1 | 1 | 0 |
| 52 | 0 | 0 | 0 | 0 | 2 | 2 | 0 | 1 | 1 | 1 | 0 |
| 53 | 0 | 0 | 1 | 0 | 2 | 2 | 0 | 1 | 0 | 1 | 0 |
| 54 | 0 | 0 | 0 | 0 | 2 | 2 | 0 | 0 | 0 | 1 | 0 |
| 55 | 0 | 0 | 2 | 1 | 2 | 2 | 0 | 0 | 0 | 1 | 0 |
| 56 | 0 | 0 | 2 | 2 | 2 | 2 | 0 | 0 | 0 | 1 | 0 |
| 57 | 0 | 0 | 0 | 1 | 2 | 2 | 0 | 0 | 0 | 1 | 0 |
| 58 | 0 | 0 | 0 | 2 | 2 | 2 | 0 | 0 | 0 | 1 | 0 |
| 59 | 0 | 0 | 0 | 0 | 2 | 2 | 0 | 0 | 0 | 0 | 0 |
| 60 | 0 | 0 | 0 | 1 | 2 | 2 | 0 | 0 | 2 | 1 | 0 |
| 61 | 0 | 0 | 0 | 1 | 2 | 2 | 0 | 2 | 0 | 1 | 0 |
| 62 | 0 | 0 | 1 | 0 | 2 | 2 | 0 | 0 | 0 | 0 | 0 |
| 63 | 0 | 0 | 0 | 0 | 2 | 2 | 0 | 0 | 0 | 0 | 0 |
| 64 | 0 | 0 | 2 | 0 | 2 | 2 | 2 | 0 | 0 | 0 | 0 |
| 65 | 0 | 0 | 2 | 0 | 2 | 2 | 0 | 0 | 0 | 0 | 0 |
| 66 | 0 | 0 | 2 | 0 | 2 | 2 | 0 | 0 | 0 | 0 | 0 |
| 67 | 0 | 0 | 0 | 1 | 2 | 2 | 2 | 0 | 0 | 0 | 1 |
| 68 | 0 | 0 | 0 | 0 | 2 | 2 | 0 | 0 | 0 | 1 | 1 |
| 69 | 0 | 0 | 0 | 0 | 2 | 2 | 0 | 0 | 0 | 2 | 1 |
| 70 | 0 | 1 | 0 | 0 | 2 | 2 | 2 | 0 | 0 | 1 | 0 |
| 71 | 0 | 0 | 0 | 1 | 2 | 2 | 2 | 0 | 0 | 1 | 0 |
| 72 | 0 | 0 | 0 | 0 | 2 | 2 | 0 | 0 | 0 | 1 | 0 |
| 73 | 0 | 0 | 1 | 0 | 2 | 2 | 0 | 0 | 0 | 0 | 0 |
| 74 | 0 | 0 | 0 | 0 | 2 | 2 | 0 | 0 | 0 | 0 | 0 |
| 75 | 0 | 0 | 2 | 0 | 2 | 2 | 0 | 0 | 0 | 0 | 0 |
| 76 | 0 | 0 | 0 | 0 | 2 | 2 | 0 | 0 | 0 | 0 | 0 |
| 77 | 0 | 0 | 0 | 0 | 2 | 2 | 0 | 0 | 0 | 0 | 0 |
| 78 | 0 | 0 | 1 | 0 | 2 | 2 | 0 | 0 | 0 | 0 | 0 |
| 79 | 0 | 0 | 1 | 0 | 2 | 2 | 2 | 0 | 0 | 0 | 0 |
| 80 | 0 | 0 | 1 | 1 | 2 | 2 | 2 | 0 | 1 | 0 | 1 |
| 81 | 0 | 0 | 2 | 0 | 2 | 2 | 2 | 0 | 0 | 0 | 0 |
| 82 | 0 | 0 | 2 | 1 | 2 | 2 | 0 | 0 | 0 | 0 | 0 |
| 83 | 0 | 0 | 1 | 0 | 2 | 2 | 0 | 0 | 0 | 0 | 0 |
| 84 | 0 | 0 | 0 | 0 | 2 | 2 | 2 | 0 | 1 | 1 | 0 |
| 85 | 0 | 0 | 2 | 0 | 2 | 2 | 2 | 0 | 0 | 1 | 0 |
| 86 | 0 | 2 | 0 | 0 | 2 | 2 | 2 | 0 | 0 | 1 | 0 |
| 87 | 0 | 0 | 0 | 0 | 2 | 2 | 2 | 0 | 1 | 1 | 0 |
| 88 | 0 | 0 | 2 | 0 | 2 | 2 | 2 | 0 | 1 | 1 | 0 |
| 89 | 1 | 0 | 0 | 1 | 2 | 2 | 0 | 0 | 1 | 1 | 0 |
| 90 | 0 | 0 | 2 | 0 | 2 | 2 | 2 | 0 | 0 | 1 | 0 |
| 91 | 0 | 0 | 1 | 1 | 2 | 2 | 2 | 2 | 0 | 1 | 0 |
| 92 | 0 | 0 | 2 | 0 | 2 | 2 | 2 | 0 | 1 | 1 | 0 |
| 93 | 0 | 0 | 0 | 0 | 2 | 2 | 2 | 0 | 1 | 1 | 0 |
| 94 | 0 | 0 | 0 | 1 | 2 | 2 | 0 | 0 | 1 | 1 | 0 |
| 95 | 0 | 0 | 0 | 0 | 2 | 2 | 0 | 0 | 1 | 1 | 0 |
| 96 | 0 | 0 | 0 | 0 | 2 | 2 | 0 | 0 | 1 | 1 | 0 |
| 97 | 0 | 0 | 0 | 0 | 2 | 2 | 2 | 0 | 0 | 0 | 0 |
| 98 | 0 | 0 | 2 | 0 | 2 | 2 | 2 | 0 | 1 | 2 | 0 |
| 99 | 0 | 0 | 0 | 0 | 2 | 2 | 2 | 0 | 0 | 2 | 0 |

TABLE VI-continued

| Comp. | PVA | AS | BCB | LN | EGT | EGP | PIP | PHI | RSI | VII | PO |
|---|---|---|---|---|---|---|---|---|---|---|---|
| 100 | 0 | 0 | 2 | 0 | 2 | 2 | 2 | 1 | 1 | 2 | 0 |
| 101 | 0 | 0 | 2 | 0 | 2 | 2 | 0 | 1 | 0 | 2 | 0 |
| 102 | 0 | 0 | 1 | 0 | 2 | 2 | 0 | 0 | 0 | 2 | 0 |
| 103 | 0 | 0 | 2 | 0 | 2 | 2 | 2 | 0 | 0 | 1 | 0 |
| 104 | 0 | 0 | 0 | 1 | 2 | 2 | 2 | 0 | 0 | 1 | 0 |
| 105 | 0 | 0 | 1 | 1 | 2 | 2 | 0 | 2 | 2 | 2 | 0 |
| 106 | 0 | 0 | 0 | 0 | 2 | 2 | 2 | 0 | 0 | 1 | 0 |
| 107 | 0 | 0 | 0 | 0 | 2 | 2 | 2 | 1 | 1 | 1 | 0 |
| 108 | 0 | 0 | 2 | 0 | 2 | 2 | 2 | 1 | 1 | 1 | 0 |
| 109 | 0 | 1 | 2 | 0 | 2 | 2 | 2 | 1 | 1 | 2 | 0 |
| 110 | 0 | 0 | 1 | 0 | 2 | 2 | 2 | 1 | 1 | 1 | 0 |
| 111 | 0 | 0 | 1 | 0 | 2 | 2 | 2 | 0 | 1 | 1 | 0 |
| 112 | 0 | 0 | 0 | 0 | 2 | 2 | 2 | 1 | 1 | 1 | 0 |
| 113 | 0 | 0 | 1 | 0 | 0 | 1 | 1 | 0 | 0 | 1 | 0 |
| 114 | 0 | 1 | 2 | 0 | 2 | 2 | 2 | 0 | 0 | 1 | 0 |
| 115 | 0 | 0 | 0 | 0 | 2 | 2 | 1 | 1 | 0 | 2 | 0 |
| 116 | 0 | 0 | 1 | 0 | 2 | 2 | 0 | 0 | 0 | 2 | 0 |
| 117 | 0 | 2 | 0 | 0 | 2 | 2 | 0 | 1 | 1 | 1 | 0 |
| 118 | 2 | 0 | 0 | 0 | 2 | 2 | 0 | 1 | 1 | 1 | 0 |
| 119 | 0 | 0 | 0 | 0 | 2 | 2 | 0 | 1 | 0 | 1 | 0 |
| 120 | 0 | 0 | 1 | 0 | 2 | 2 | 0 | 0 | 1 | 1 | 0 |
| 121 | 0 | 0 | 0 | 0 | 2 | 2 | 0 | 0 | 0 | 0 | 0 |
| 122 | 0 | 0 | 0 | 0 | 2 | 2 | 0 | 0 | 0 | 0 | 2 |
| 123 | 0 | 0 | 0 | 0 | 2 | 2 | 0 | 0 | 0 | 0 | 1 |
| 124 | 0 | 0 | 0 | 0 | 2 | 2 | 2 | 0 | 0 | 0 | 0 |
| 125 | 0 | 0 | 0 | 0 | 2 | 2 | 0 | 1 | 0 | 1 | 0 |
| 126 | 0 | 0 | 0 | 0 | 2 | 2 | 0 | 0 | 0 | 1 | 0 |
| 127 | 0 | 0 | 0 | 0 | 2 | 2 | 0 | 0 | 0 | 1 | 0 |
| 128 | 0 | 2 | 0 | 0 | 2 | 2 | 0 | 0 | 0 | 1 | 0 |
| 129 | 0 | 0 | 0 | 0 | 2 | 2 | 0 | 0 | 0 | 1 | 0 |
| 130 | 0 | 0 | 0 | 0 | 2 | 2 | 2 | 0 | 0 | 1 | 0 |
| 131 | 0 | 0 | 0 | 0 | 2 | 2 | 0 | 0 | 0 | 1 | 0 |
| 132 | 0 | 0 | 0 | 0 | 2 | 2 | 0 | 0 | 0 | 1 | 0 |
| 133 | 0 | 0 | 0 | 0 | 2 | 2 | 0 | 0 | 0 | 1 | 0 |
| 134 | 0 | 0 | 0 | 0 | 2 | 2 | 0 | 0 | 0 | 0 | 0 |
| 135 | 0 | 0 | 0 | 1 | 2 | 2 | — | 2 | 2 | 1 | 0 |
| 136 | 0 | 0 | 0 | 0 | 2 | 2 | — | 2 | 2 | 0 | 0 |
| 137 | 0 | 0 | 0 | 2 | 2 | 2 | 0 | 2 | 2 | 1 | 0 |
| 138 | 0 | 0 | 0 | 0 | 0 | 0 | 2 | 0 | 0 | 0 | 0 |
| 139 | 0 | 0 | 0 | 1 | 2 | 2 | 0 | 2 | 0 | 2 | 0 |
| 140 | 0 | 0 | 0 | 1 | 2 | 2 | 0 | 2 | 2 | 2 | 0 |
| 141 | 0 | 0 | 0 | 1 | 2 | 2 | 0 | 2 | 2 | 2 | 0 |
| 142 | 0 | 0 | 0 | 0 | 2 | 2 | 1 | 2 | 2 | 2 | 0 |
| 143 | 0 | 0 | 0 | 0 | 2 | 2 | 0 | 0 | 0 | 0 | 0 |
| 181 | 0 | 0 | 0 | 0 | 2 | 2 | 2 | 0 | 0 | 0 | 0 |
| 182 | 0 | 0 | 1 | 1 | 2 | 2 | 0 | 1 | 2 | 2 | 0 |
| 183 | 0 | 0 | 0 | 0 | 2 | 2 | 1 | 1 | 2 | 2 | 0 |
| 184 | 0 | 0 | 2 | 0 | 2 | 2 | 0 | 1 | 2 | 2 | 0 |
| 185 | 0 | 1 | 1 | 0 | 2 | 2 | 0 | 0 | 0 | 0 | 0 |
| 186 | 0 | 0 | 0 | 0 | 0 | 2 | 0 | 0 | 0 | 0 | 0 |
| 189 | 0 | 0 | 0 | 0 | 2 | 2 | 1 | 0 | 0 | 1 | 0 |
| 190 | 1 | 0 | 0 | 0 | 0 | 1 | 2 | 0 | 0 | 0 | 0 |
| 191 | 0 | 0 | 0 | 0 | 0 | 2 | 0 | 0 | 0 | 0 | 0 |
| 213 | 0 | 2 | 2 | 0 | 2 | 2 | 2 | 0 | 0 | 0 | 1 |

Evaluation of In Vivo Fungicidal Activity of Test Compounds

Test compounds are dissolved in acetone and diluted with deionized water containing about 0.05% TWEEN 20®, a polyoxyethylens sorbitan monolaurate surfactant manufactured by Atlas Chemical Industries, to give a concentration of 400 ppm. Subsequent dilutions are made with an 0.05% aqueous solution of TWEEN 20®.

Most plants are sprayed with test solution, dried and inoculated with fungi. When disease symptom development is optimal, the plants are rated for disease control according to the rating scale shown below. Each test contains inoculated treated plants, inoculated untreated plants and a reference standard. When more than one test is run, the data are averaged. The data obtained are shown in Table V1a.

RATING SCALE

| Rating | Range % Control |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| — | no evaluation |

PHYTOPATHOGENIC FUNGI

| Symbol | Disease | Pathogen |
|---|---|---|
| AS | Apple Scab | *Venturia inaequalis* |
| GDM | Grape Downy Mildew | *Plasmopara viticola* |
| PB | Pepper Botrytis | *Botrytis cinerea* |
| RB | Rice Blast | *Pyricularia oryzae* |
| SBC | Sugar Beet Cercospora | *Cercospora beticola* |
| TEB | Tomato Early Blight | *Alternaria solani* |
| WBM | Wheat Powdery Mildew | *Erysiphe graminis* f. sp. *tritici* |
| WSN | Wheat Blotch | *Septoria nodorum* |

TABLE VIa

| Comp. | AS | GDM | PB | RB | SBC | TEB | WPM | WSN |
|---|---|---|---|---|---|---|---|---|
| 187 | 4 | 5 | 7 | 0 | 5 | 6 | 9 | 7 |
| 188 | 5 | 0 | 5 | 0 | 4 | 0 | 8 | 6 |
| 192 | 7 | 6 | 8 | 0 | 7 | 4 | 7 | 7 |
| 193 | 6 | 8 | 7 | 0 | 6 | 2 | 8 | 3 |
| 194 | 6 | 7 | 4 | 0 | 8 | 3 | 7 | 7 |
| 195 | 6 | 5 | 5 | 7 | 7 | 0 | 7 | 7 |
| 196 | 5 | 5 | 5 | 6 | 8 | 0 | 9 | 7 |
| 197 | 5 | 7 | 8 | 0 | 7 | 0 | 8 | 7 |
| 198 | 6 | 6 | 7 | 0 | 8 | 6 | 8 | 8 |
| 199 | 6 | 5 | 7 | 0 | 3 | 4 | 8 | 7 |
| 200 | 7 | 5 | 8 | 0 | 8 | 0 | 8 | 8 |
| 201 | 6 | 7 | 3 | 0 | 6 | 0 | 8 | 5 |
| 202 | 6 | 5 | 7 | 0 | 7 | 0 | 8 | 5 |
| 203 | 0 | 0 | 8 | 0 | 8 | 6 | 8 | 6 |
| 204 | 0 | 0 | 8 | 0 | 7 | 6 | 7 | 6 |

Evaluation of In Vitro Fungicidal Activity of Test Compounds

Test compounds are dissolved in acetone and dispersed into cell well plates containing a suspension of ground fungal mycelium in a nutrient broth. Assay plates are incubated for 3-4 days at 21° C. Growth inhibition is measured visually and is rated using the following scale:

| Rating | % Inhibition |
|---|---|
| 0 | 0 |
| 1 | 1–29 |
| 3 | 30–59 |
| 5 | 60–89 |
| 7 | 90–99 |
| 9 | 100 |

Untreated controls, solvent blanks and reference standards are included in each test.
Assay fungi include the following pathogens:

| SYMBOL | PATHOGEN |
|---|---|
| FUS OXC | *Fusarium oxysporium* f. sp. *cucumerinum* |
| PSDC HE | *Pseudocercosporella herpotrichoides* |
| PTYH UL | *Pythium ultimum* |
| RHIZ SO | *Rhizoctonia solani* |

| FUS OXC | PSDC HE | PYTH UL | RHIZ SO |
|---|---|---|---|
| 0 | 7 | 5 | 5 |
| 0 | 0 | 7 | 5 |
| 0 | 0 | 7 | 5 |
| 0 | 0 | 7 | 3 |
| 0 | 5 | 7 | 7 |
| 0 | 0 | 7 | 3 |
| 0 | 0 | 7 | 7 |
| 0 | 0 | 7 | 7 |
| 1 | 7 | 7 | 7 |
| 0 | 0 | 3 | 3 |
| 0 | 5 | 7 | 7 |
| 0 | 5 | 7 | 7 |
| 0 | 7 | 7 | 7 |
| 0 | 0 | 1 | 3 |
| 0 | 1 | 0 | 1 |

I claim:

1. A process for the preparation of a compound of the general formula I,

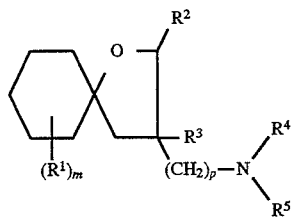

or an acid-addition salt thereof, in which $R^1$ or each $R^1$ independently represents an optionally substituted alkyl, cycloalky, cycloalkylalkyl, alkoxy, cycloalkoxy, alkoxyalkyl, aralkyl, aryl or aryloxy group, or $R^1$ or each $R^1$, together with the ring to which they are attached, represents an optionally substituted polycyclic hydrocarbyl group, $R^2$ represents a hydrogen atom or a $C_{1-4}$ alkyl group, $R^3$ represents a hydrogen atom, $R^4$ and $R^5$ each independently represent a hydrogen atom, an optionally substituted alkyl, alkenyl, alkynyl, cycloalkylalkyl, cycloalky, bicycloalkyl, tricycloalkyl, alkoxyalkyl, aryl, aralkyl, haloaralkyl, a 4- to 6- membered heterocyclyl, tetrahydrofurfuryl or dioxolanyl group, or $R^4$ and $R^5$ together represent and optionally substituted, saturated or unsaturated carbon chain which may optionally contain one or more oxygen atoms and which may optionally be aryl- or cycloalkyl fused, m represents zero or an integer from 1 to 6, and p represents zero which process comprises reaction of a compound of general formula II

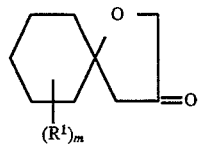

in which $R^1$ and m are as defined hereinbefore, with a compound of the general formula III

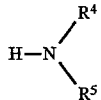

in which $R^4$ and $R^5$ are as defined hereinbefore, under reducing conditions.

* * * * *